United States Patent
Bronstein et al.

[11] Patent Number: 5,831,102
[45] Date of Patent: Nov. 3, 1998

[54] CHEMILUMINESCENT 3-(SUBSTITUTED ADAMANT-2'-YLIDENE) 1,2-DIOXETANES

[75] Inventors: Irena Y. Bronstein, Newton; Brooks Edwards, Cambridge; Rouh-Rong Juo, Alston, all of Mass.

[73] Assignee: Tropix, Inc., Bedford, Mass.

[21] Appl. No.: 598,353

[22] Filed: Feb. 8, 1996

Related U.S. Application Data

[60] Continuation of Ser. No. 233,085, Apr. 25, 1994, Pat. No. 5,543,295, which is a division of Ser. No. 806,928, Dec. 12, 1991, Pat. No. 5,330,900, which is a division of Ser. No. 574,786, Aug. 30, 1990, Pat. No. 5,112,960.

[51] Int. Cl.$^6$ .................................................. C07D 321/00
[52] U.S. Cl. ................................ 549/332; 435/6; 435/7.1; 435/21; 435/810; 436/172; 436/800; 436/808; 549/200; 549/201; 549/218; 549/330; 549/510; 549/511; 560/1; 560/18; 560/19; 560/22; 560/64; 560/66; 568/8; 568/300; 568/579; 568/580; 568/583; 568/628; 568/659; 568/662; 568/663; 568/700; 568/701; 568/704; 568/715; 570/101; 570/102; 570/123; 570/127; 570/140; 570/181; 570/182; 570/183; 935/77; 935/78
[58] Field of Search ..................... 435/6, 21, 7.1, 435/968, 810; 436/800, 808, 172; 935/78, 77; 549/200, 201, 218, 330, 332, 510, 511; 560/1, 8, 19, 22, 64, 66; 568/8, 300, 579, 580, 583, 628, 659, 662, 663, 700, 701, 704, 715; 570/101, 102, 123, 127, 140, 181–183

[56] References Cited

U.S. PATENT DOCUMENTS

| | | | |
|---|---|---|---|
| 4,931,223 | 6/1990 | Bronstein et al. | 252/700 |
| 4,952,707 | 8/1990 | Edwards et al. | 549/221 |

(List continued on next page.)

*Primary Examiner*—Ardin H. Marschel
*Attorney, Agent, or Firm*—Oblon, Spivak, McClelland, Maier & Neustadt, P.C.

[57] ABSTRACT

Enzymatically cleavable chemiluminescent 1,2-dioxetane compounds capable of producing light energy when decomposed, substantially stable at room temperature before a bond by which an enzymatically cleavable labile substituent thereof is intentionally cleaved, are disclosed. These compounds can be represented by the formula:

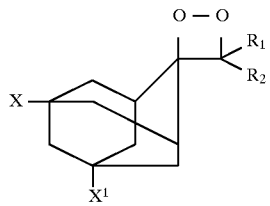

wherein:
X and $X^1$ each represent, individually, hydrogen, a hydroxyl group, a halo substituent, an unsubstituted lower alkyl group, a hydroxy (lower) alkyl group, a halo (lower) alkyl group, a phenyl group, a halophenyl group, an alkoxyphenyl group, a hydroxyalkoxy group, a cyano group or an amide group, with at least one of X and $X^1$ being other than hydrogen; and $R_1$ and $R_2$, individually or together, represent an organic substituent that does not interfere with the production of light when the dioxetane compound is enzymatically cleaved and that satisfies the valence of the dioxetane compound's 4-carbon atom, with the provisos that if $R^1$ and $R_2$ represent individual substituents the $R_2$ substituent is aromatic, heteroaromatic, or an unsaturated substituent in conjugation with an aromatic ring, and that at least one of $R_1$ and $R_2$ is, or $R_1$ and $R_2$ taken together are, an enzymatically cleavable labile group-substituted fluorescent chromophore group that produces a luminescent substance when the enzymatically cleavable labile substituent thereof is removed by an enzyme.

The corresponding dioxetanes which, instead of being substituted at the 5' or 7', or at the 5' and 7' positions, instead contain a 4' methylene group, are also disclosed, as are intermediates for all these 3-substituted adamant-2'-ylidene-dioxetanes, and their use as reporter molecules in assays.

16 Claims, 17 Drawing Sheets

U.S. PATENT DOCUMENTS

| | | | |
|---|---|---|---|
| 4,956,477 | 9/1990 | Bronstein et al. | 549/221 |
| 4,978,614 | 12/1990 | Bronstein | 435/21 |
| 5,089,630 | 2/1992 | Bronstein et al. | 549/220 |
| 5,112,960 | 5/1992 | Bronstein et al. | 536/18.1 |
| 5,145,772 | 9/1992 | Voyta et al. | 435/4 |
| 5,177,241 | 1/1993 | Bronstein et al. | 558/194 |
| 5,220,005 | 6/1993 | Bronstein | 536/26.21 |
| 5,326,882 | 7/1994 | Bronstein et al. | 549/16 |
| 5,330,900 | 7/1994 | Bronstein et al. | 435/6 |
| 5,336,596 | 8/1994 | Bronstein et al. | 435/6 |

CHEMILUMINESCENT 3-(SUBSTITUTED ADAMANT-2'-YLIDENE) 1,2-DIOXETANES

This application is a continuation of U.S. patent application Ser. No. 08/233,085, filed Apr. 25, 1994, now U.S. Pat. No. 5,543,295, which a divisional of U.S. patent application Ser. No. 07/806,928, filed Dec. 12, 1991, now U.S. Pat. No. 5,330,900 which is a divisional of U.S. patent application Ser. No. 07/574,786, filed Aug. 30, 1990, now U.S. Pat. No. 5,112,960.

FIELD OF THE INVENTION

This invention relates to improved chemiluminescent 1,2-dioxetane compounds. More particularly, this invention relates to improved enzymatically cleavable chemiluminescent 1,2-dioxetane compounds that contain enzymatically removable labile groups. Such labile groups prevent the molecule from decomposing to produce light, i.e., visible light or light detectable by appropriate instrumentation, until an appropriate enzyme is added to remove the labile group.

One enzyme molecule will effect the removal, through a catalytic cycle, of its complementary labile group from thousands of enzymatically cleavable chemiluminescent 1,2-dioxetane molecules. This is in marked contrast to the situation with chemically cleavable chemiluminescent 1,2-dioxetanes, where one molecule of chemical cleaving agent is needed to remove the complementary labile group from each dioxetane molecule. For example, one mole of sodium hydroxide is needed to cleave one mole of hydrogen ions from the hydroxyl substituent on the phenyl group in 3-(2'-spiro-adamantane)-4-methoxy-4-(3"-hydroxy)phenyl-1,2-dioxetane, while only a single mole of alkaline phosphatase ("AP") is needed to cleave the phosphoryloxy group in 1,000–5,000 moles of 3-(2'-spiroadamantane)-4-methoxy-4-(3" phosphoryloxy)phenyl-1,2-dioxetane disodium salt per second; see Jablonski, "DNA Probes for Infectious Diseases" (Boca Raton, Fla.:CRC Press, 1989), p. 22.

Enzymatically cleavable light-producing 1,2-dioxetane compounds will usually also contain stabilizing groups, such as an adamantylidene group spiro bonded to the dioxetane ring's 3-carbon atom, that will aid in preventing the dioxetane compound from undergoing substantial decomposition at room temperature (about 25° C.) before the bond by which the enzymatically cleavable labile group is attached to the remainder of the molecule is intentionally cleaved, a concept introduced to 1,2-dioxetane chemistry by Wierynga, et al., *Tetrahedron Letters*, 169 (1972) and McCapra, et al., *J.Chem.Soc., Chem.Comm.*, 944 (1977). These stabilizing groups thus permit such dioxetanes to be stored for acceptably long periods of time before use, e.g., for from about 12 months to as much as about 12 years at temperatures ranging from about 4° to about as much as 30° C., without undergoing substantial decomposition.

This invention further relates to the incorporation of its dioxetane molecules in art-recognized immunoassays, chemical assays and nucleic acid probe assays, and to their use as direct chemical/physical probes for studying the molecular structures or microstructures of various macromolecules, synthetic polymers, proteins, nucleic acids, catalytic antibodies, and the like, to permit an analyte—the chemical or biological substance whose presence, amount or structure is being determined—to be identified or quantified.

BACKGROUND OF THE INVENTION

Chemiluminescent 1,2-dioxetanes have assumed increasing importance in recent years, particularly with the advent of the enzymatically cleavable chemiluminescent 1,2-dioxetanes disclosed in Bronstein U.S. patent application Ser. No. 889,823, filed Jul. 24, 1986 (the "'823 application"); Bronstein, et al. U.S. patent application Ser. No. 140,035, filed Dec. 31, 1987; Edwards U.S. patent application Ser. No. 140,197, filed Dec. 31, 1987 (the "'197 application") and Edwards, et al. U.S. patent application Ser. No. 213,672 ("'672 application"), filed Jun. 30, 1988.

Again in marked contrast to enzymatically cleavable 1,2-dioxetanes, the various chemically cleavable chemiluminescent 1,2-dioxetanes known up to now have had little if any utility as reporter molecules in any type of analytical technique, and certainly not in bioassays. This is because the known chemically cleavable compounds are for the most part water insoluble—except for certain acetoxy-substituted 1,2-dioxetanes that are somewhat water-soluble as well as organic solvent-soluble—and thus may not be useful in biological assays unless they could somehow be modified by adding to them groups or substituents that allow conjugation to a biological species, e.g., an antibody, thus permitting such conjugated chemically cleavable 1,2-dioxetanes to be used as chemically activated chemiluminogenic labels.

The water solubility of typical enzymatically cleavable chemiluminescent 1,2-dioxetanes, on the other hand—e.g., adamantyl-appended enzymatically cleavable 1,2-dioxetanes that decompose in the presence of a suitable enzyme with light emission, such as 3-(4-methoxyspiro[1,2-dioxetane-3,2'-tricyclo[3.3.1.1$^{3,7}$]decan]-4-yl)phenyl phosphate and its salts, e.g., the disodium salt, identified hereinbelow in shorthand fashion as adamantylidenemethoxyphenoxyphosphorylated dioxetane ("AMPPD"), and 3-(4-methoxyspiro[1,2-dioxetane-3,2'-tricyclo[3.3.1.1$^{3,7}$]decan]-4-yl)phenyloxy-3"-β-D-galactopyranoside and its salts ("AMPGD")—makes them eminently suitable for use as reporter molecules in many types of analytical techniques carried out in aqueous media, and especially in bioassays.

It has been observed that AMPPD in aqueous solution, and also in the presence of chemiluminescence enhancers, e.g., a polymeric ammonium, phosphonium or sulfonium salt such as poly[vinylbenzyl(benzyldimethylammonium chloride)] ("BDMQ") and other heteropolar polymers (see Voyta, et al. U.S. patent application Ser. No. 203,263, filed Jun. 1, 1988), exhibits longer than optimum periods of time to reach constant light emission characteristics ("t½", defined as the time necessary to attain one half of the maximum chemiluminescence intensity at constant, steady-state light emission levels; this emission half-life varies as a function of the stability of the dioxetane oxyanion in various environments).

Statistically, approximately seven t½ periods are required to reach steady-state light emission kinetics. The t½ for AMPPD at concentrations above $2 \times 10^{-5}$M in aqueous solution at pH 9.5 in the presence of BDMQ has been found to be 7.5 minutes. At $4 \times 10^{-3}$M in the absence of BDMQ the t½ has been found to be approximately 30–60 minutes, while at $2 \times 10^{-5}$M in aqueous solution the t½ for AMPPD has been found to be 2.5 minutes.

In rapid bioassays that employ enzymatically cleavable chemiluminescent 1,2-dioxetanes as reporter molecules it is desirable to reach steady-state light emission kinetics as quickly as possible so as to detect an "endpoint" in the assay. And while chemiluminescence intensity can be measured before achieving steady-state kinetics, sophisticated, thermally controlled luminometry instrumentation must be used if one wishes to acquire precise data prior to steady-state emission kinetics.

Furthermore, AMPPD, in aqueous buffered solution both in the presence and the absence of chemiluminescence enhancers such as BDMQ, exhibits higher than desirable thermal and nonenzymatically activated light emission, or "noise". Such noise can be attributed to emissions from the excited states of adamantanone and of the methyl m-oxybenzoate anion derived from the aromatic portion of the AMPPD molecule. This noise can limit the levels of detection, and thus prevent the realization of ultimate sensitivity, as the measured noise level of AMPPD is approximately two orders of magnitude above the dark current in a standard luminometer.

Enzymatic cleavage of AMPPD with alkaline phosphatase also generates anionic, dephosphorylated AMPPD—adamantylidenemethoxymethylphenolate dioxetane, or "AMP$^-$D". This phenolate anion can also be formed hydrolytically in small amounts, giving rise to a background chemiluminescence signal which, in an organized molecular assembly, such as a micelle, liposome, lamellar phase, thin layer, lipid bilayer, liposome vesicle, reversed micelle, microemulsion, microgel, latex, membrane or polymer surface, and in a hydrophobic environment such as that produced by a chemiluminescence enhancer, e.g., BDMQ, can generate strong, enhanced levels of light emission, thereby creating high background signals and substantially lowering the dynamic range of the signal resulting from enzymatic hydrolysis of AMPPD.

Consistent with the above-described observations, we have postulated the following mechanisms.

In the presence of enhancing polymers such as BDMQ:
1. Enzymatic Pathway (AP present):

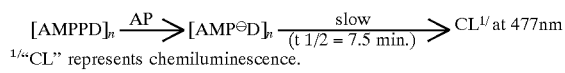

[1]"CL" represents chemiluminescence.

2. Thermal Pathway (no AP present):

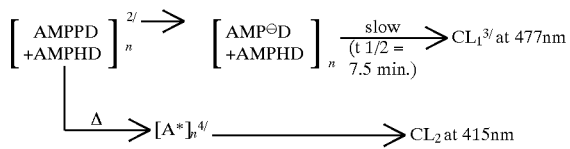

[2]AMPPD in aqueous buffered solution contains a small amount of dephosphorylated, hydroxylated 1,2-dioxetane ("AMPHD"). If the solution pH is sufficiently high (above about 9.5), the dephosphorylated dioxetane may be present in the anionic state as AMP$^-$D.

[3]"CL$_1$" and "CL$_2$" represent background chemiluminescence.

[4]"A*" represents adamantanone in the excited energy state.

Even in the absence of enhancing polymer, AMPPD can exist in aqueous solution as an aggregate:

3. Enzymatic Pathway:

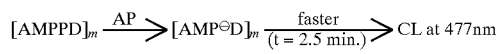

4. Thermal and Hydrolytic Pathway:

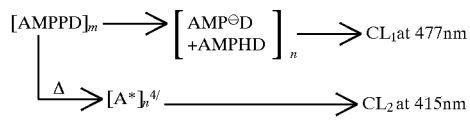

In the above mechanisms, n>>>m; n and m are a function of the presence or absence of enhancing polymer, and AMPPD concentration.

The excited state of the adamantanone singlet in aggregate form (n or m>1) may exhibit higher yields of signal emission, here again particularly if "stabilized" to emit more light, as by the presence of a chemiluminescence enhancer such as BDMQ, than does the excited energy state of unaggregated adamantanone. This is perhaps due to the former's having lower singlet states, lower yields of intersystem crossing or slower intersystem crossing than the latter, or to other as yet unknown factors. Since luminometers, generally, are designed to detect all photons emitted regardless of their energy, or their wavelength, 415 nm and 477 nm chemiluminescence are both detected as background noise emissions. Similarly, when photographic or X-ray film is used to record chemiluminescence, no discrimination between the different wavelength emissions can easily be made, thus, sensitivity of detection is limited by background noise.

Finally, the observed aggregation of AMPPD under the conditions described above may result from the amphiphilic nature of AMPPD, or its phenolate anion, and like molecules:

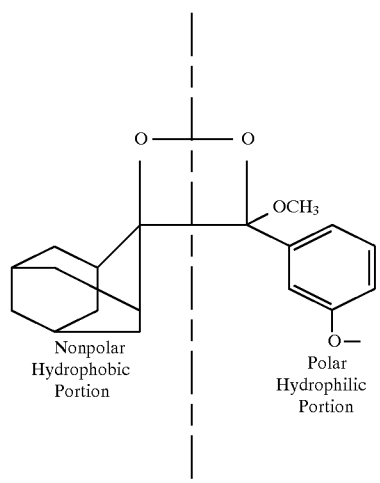

It is, therefore, an object of this invention to decrease the time necessary to conduct assays, and particularly bioassays, in which enzymatically cleavable chemiluminescent 1,2-dioxetanes are used as reporter molecules.

It is also an object of this invention to provide new and improved enzymatically cleavable chemiluminescent 1,2-dioxetanes which, when used as reporter molecules in assays, and particularly bioassays, reduce the time required to complete the assay.

A further object of this invention is to provide new and improved enzymatically cleavable chemiluminescent 1,2-dioxetanes for use as substrates for enzyme-based assays, and particularly bioassays, which provide improved signal to background behavior and thus provide improved detection levels.

A still further object of this invention is to provide novel intermediates useful in synthesizing these improved enzymatically cleavable 1,2-dioxetanes.

Another object of this invention is to provide methods of preparing these enzymatically cleavable chemiluminescent 1,2-dioxetanes and intermediates therefor.

These and other objects, as well as the nature, scope and utilization of this invention, will become readily apparent to those skilled in the art from the following description and the appended claims.

SUMMARY OF THE INVENTION

This invention provides a new class of stable, enzymatically cleavable chemiluminescent 3-(substituted adamant-2'-ylidene)-1,2-dioxetane compounds capable of reacting in aqueous media, e.g., in a sample of biological fluid in solution or on a solid surface, e.g., a membrane surface such as a nylon membrane, with an enzyme or enzyme modified specific binding pair to release optically detectable energy.

In aqueous media these modified admantylidene dioxetanes enable assays in which they are used as reporter molecules to be conducted faster and with greater sensitivity than hitherto possible using AMPPD.

While we do not wish to be bound by any mechanism or theory advanced to explain this unexpectedly superior behavior, it may be that the presence of substituents of the type disclosed herein on or in the adamantylidene moiety prevents the dioxetane molecules from packing efficiently, and thus prevents them from forming "stabilized" organized assemblies, whether in the form of micelles or some other aggregated state. Certain of these substituents may also hydrogen bond to other substances in their aqueous environment, including water itself, thereby further preventing aggregate formation. And, it is also possible that electronic and dipole effects may contribute to this phenomenon, as evidenced by shorter t½'s and lower background noise.

DETAILED DESCRIPTION OF THE INVENTION

Figure 1:
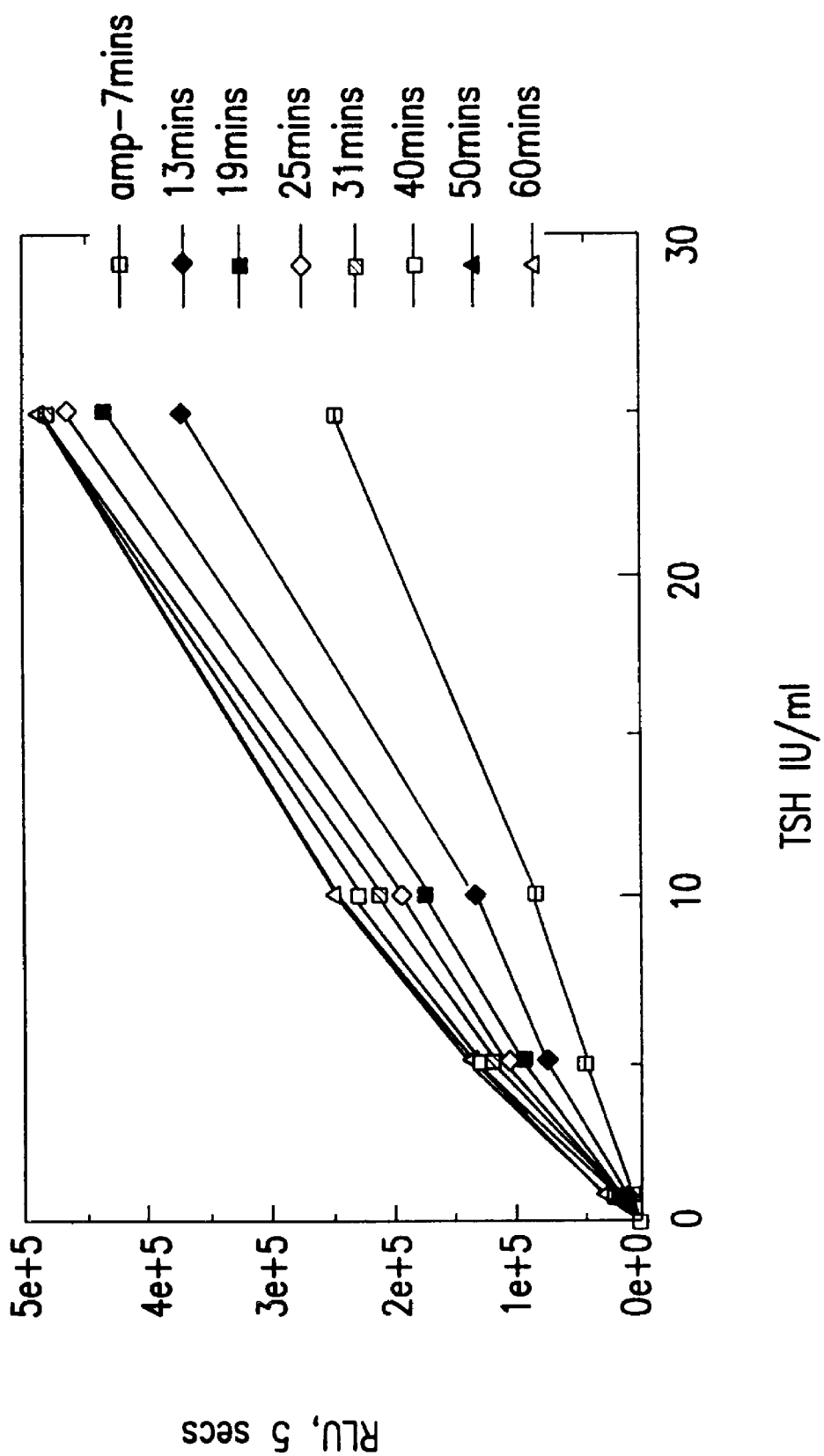
FIGS. 1–5 show TSH, RLV v. TSH for each of AMPPD and its bromo-, B-hydroxy-,A-hydroxy- and chloroadamant-2'-ylidene analogs, respectively, obtained as described in Example XII below.
Figure 2:
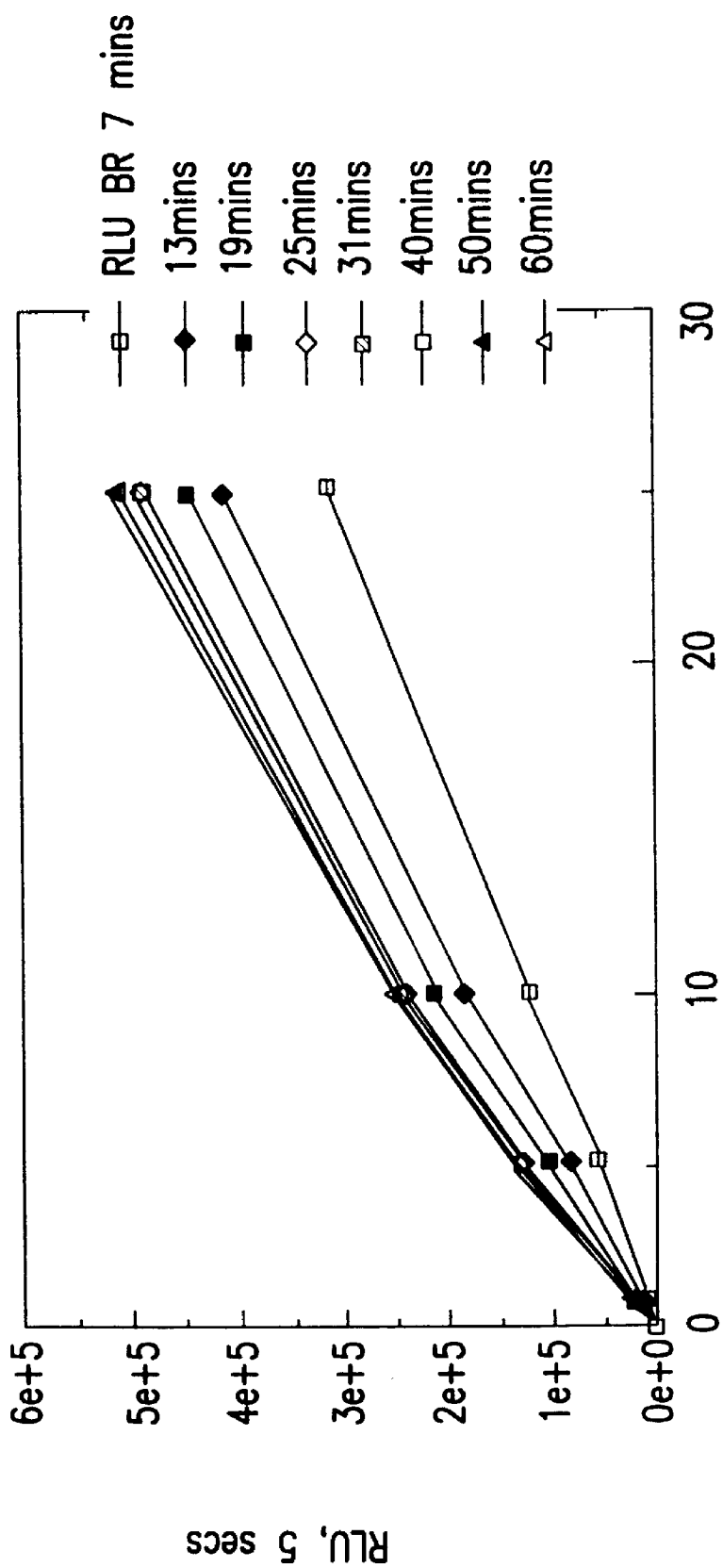
Figure 3:
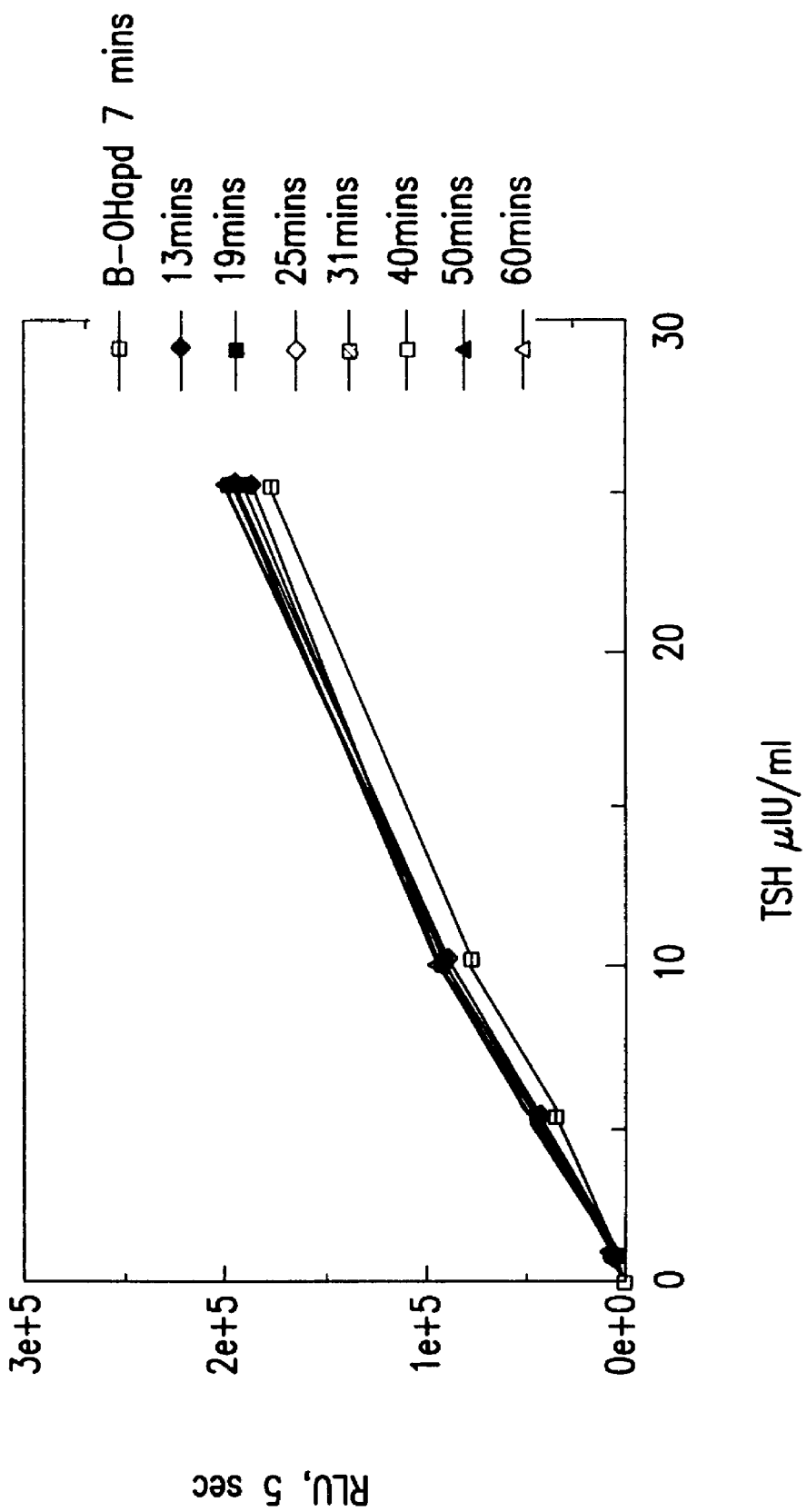
Figure 4:
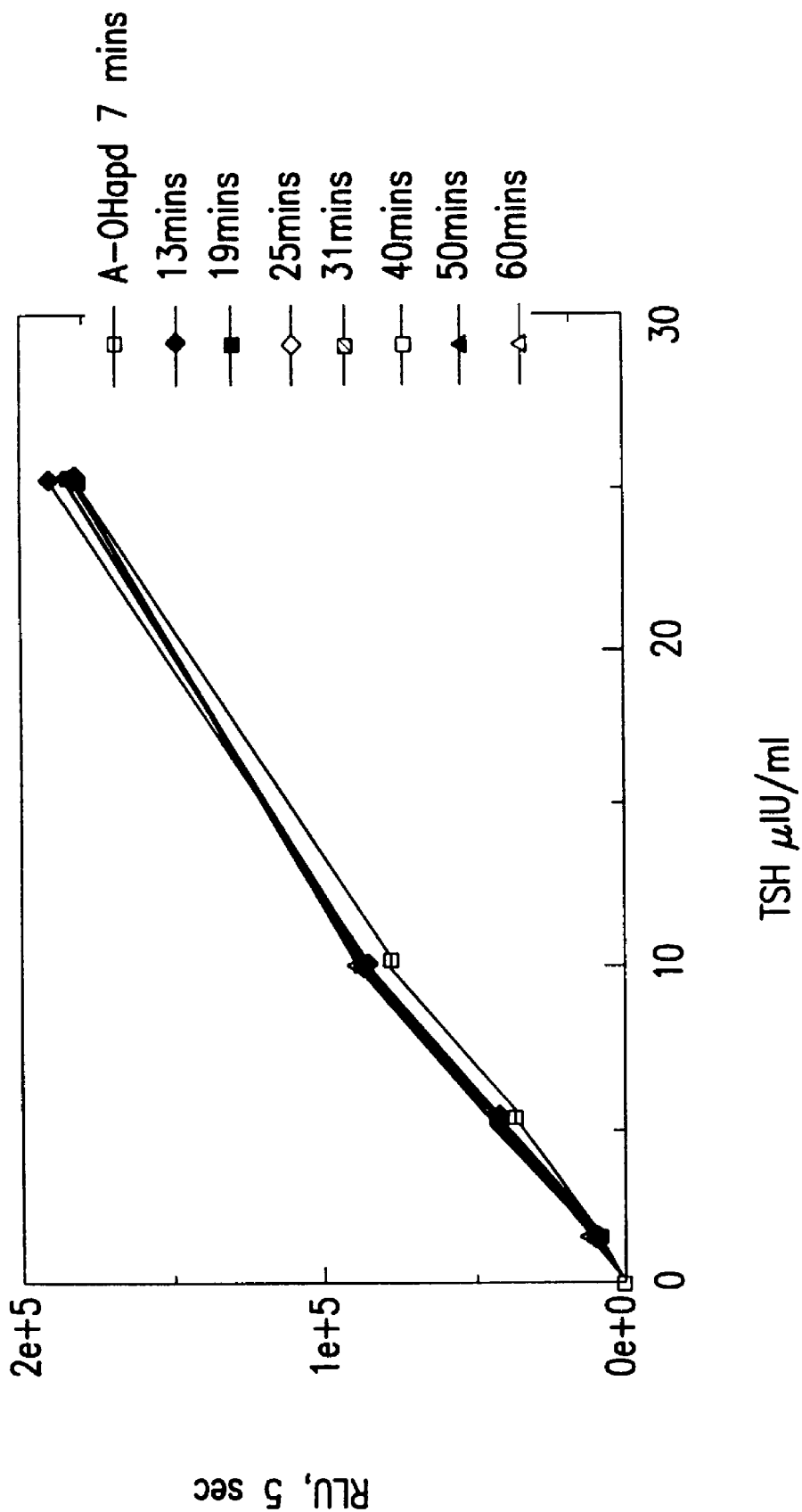
Figure 5:
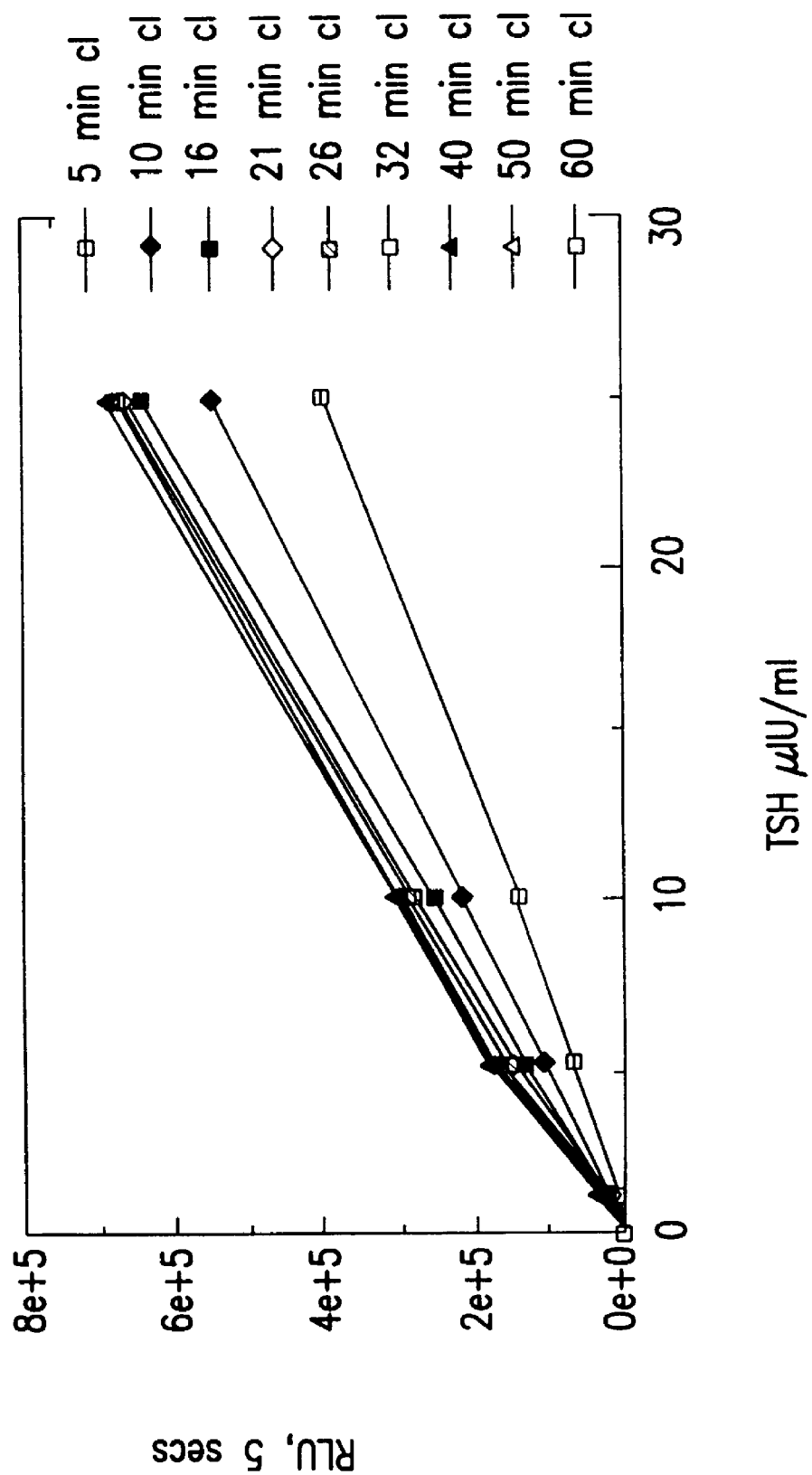
Figure 6:
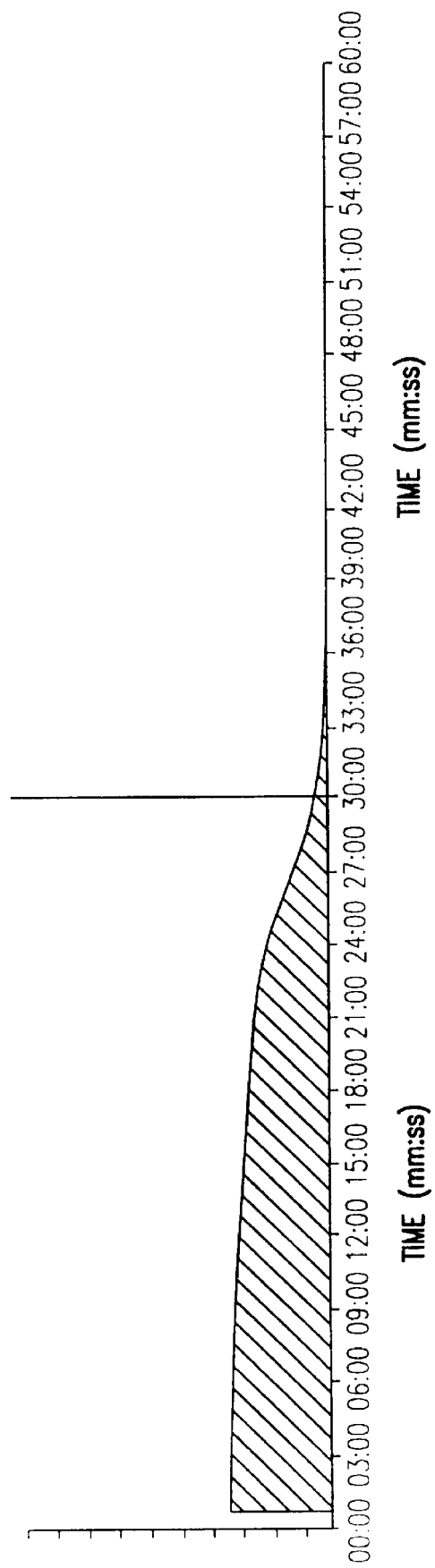
FIGS. 6–10 compare the total luminescence emissions obtained from AMPPD and its A-hydroxy-, B-hydroxy, chloro- and bromoadamant-2'-ylidene analogs, respectively, obtained as described in Example XIII below.
Figure 7:
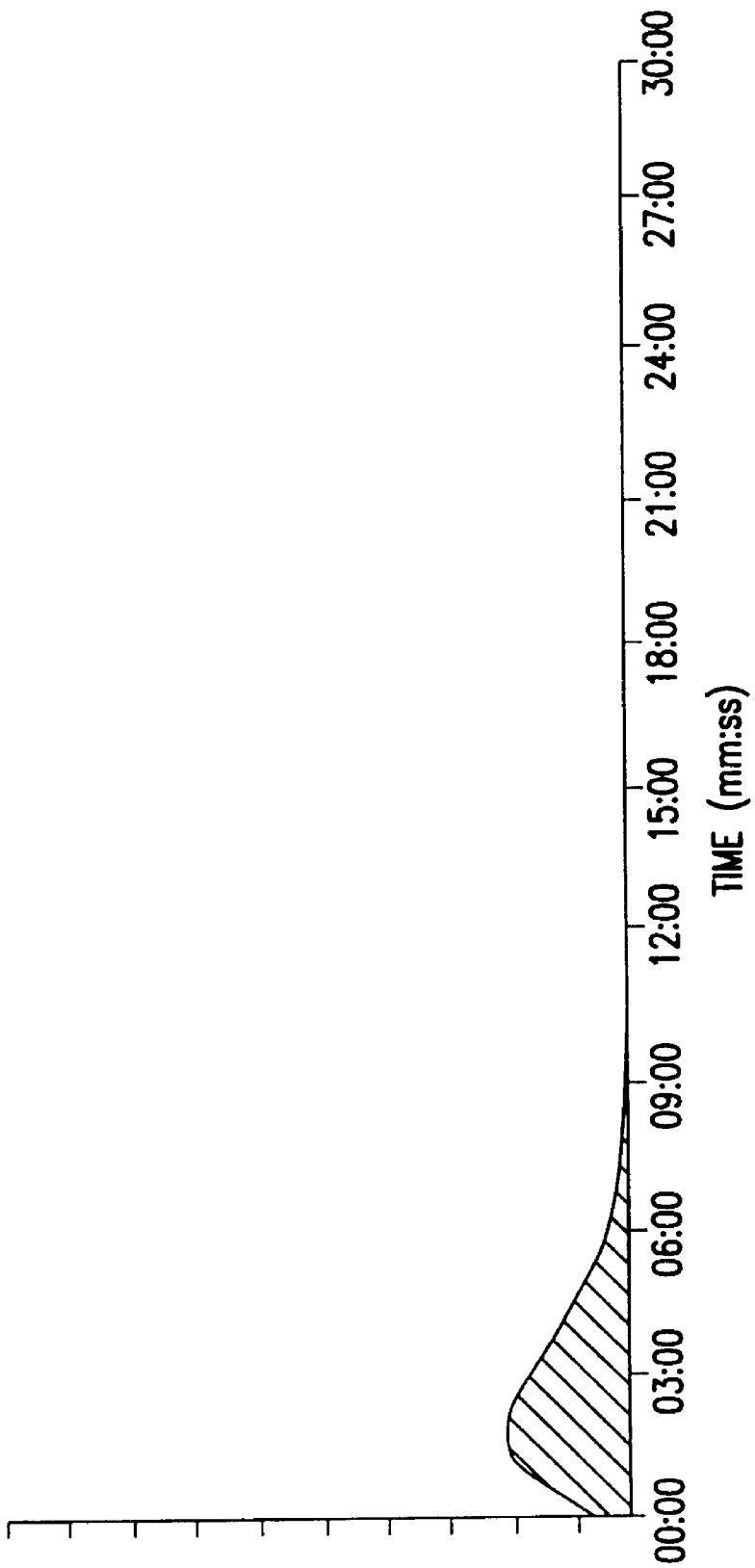
Figure 8:
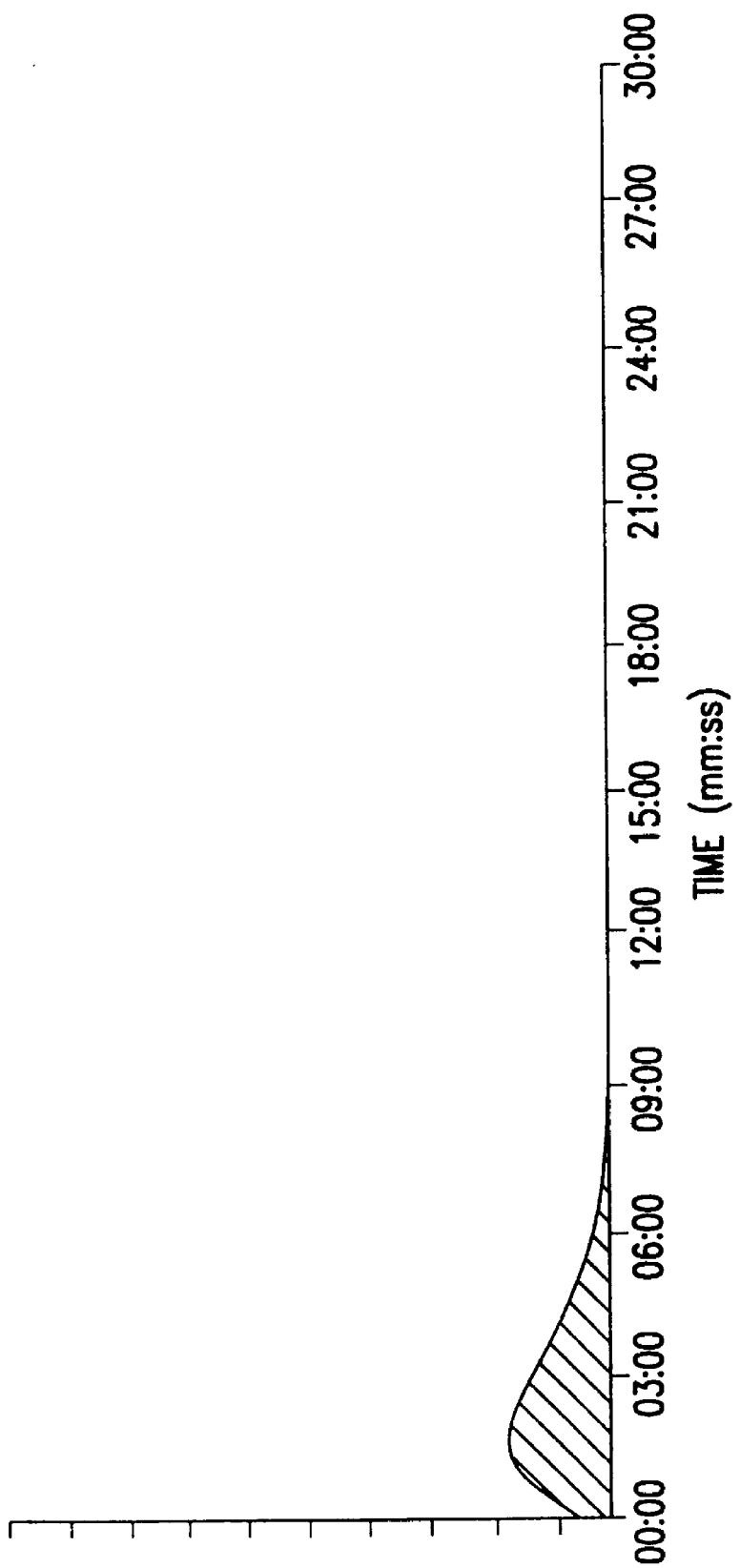
Figure 9:
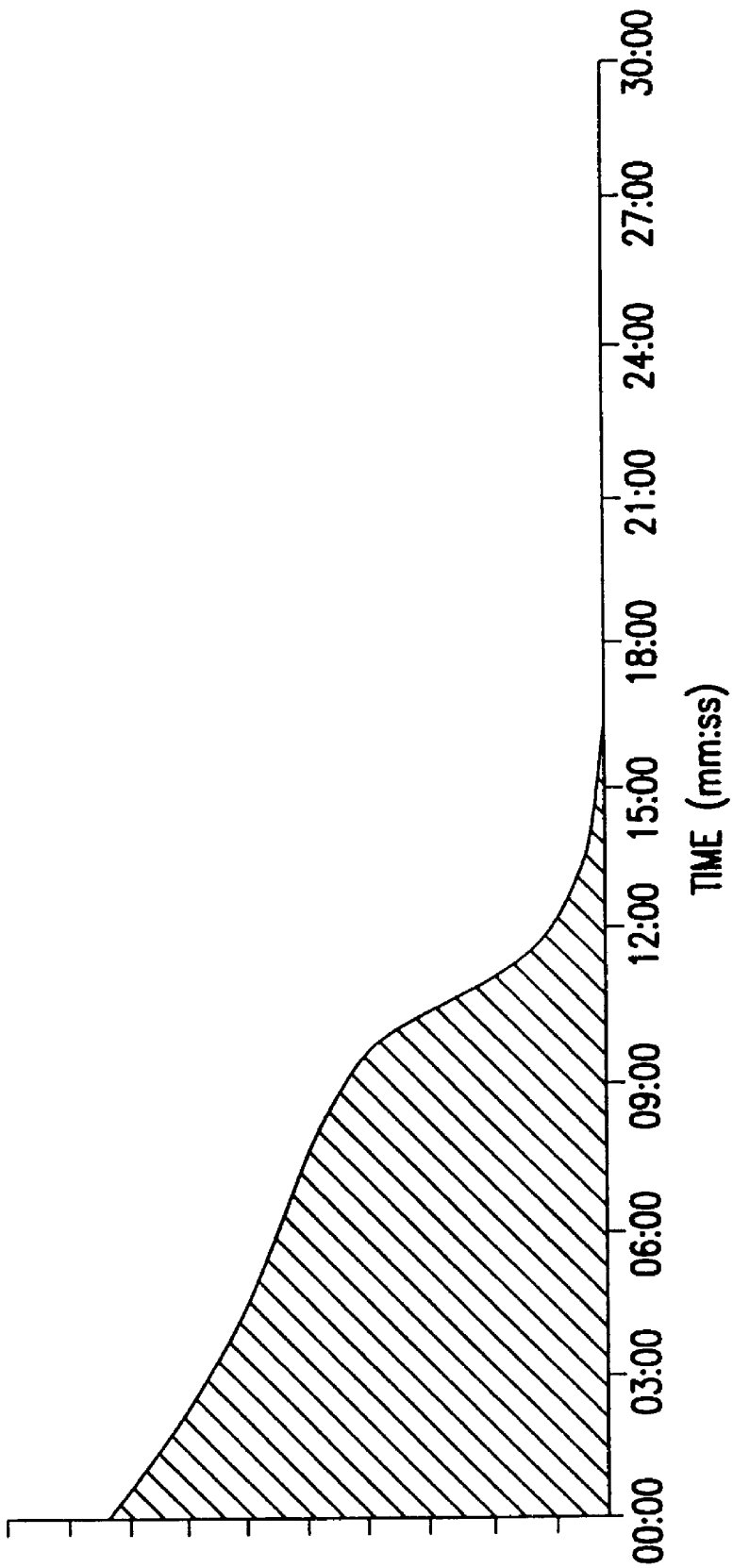
Figure 10:
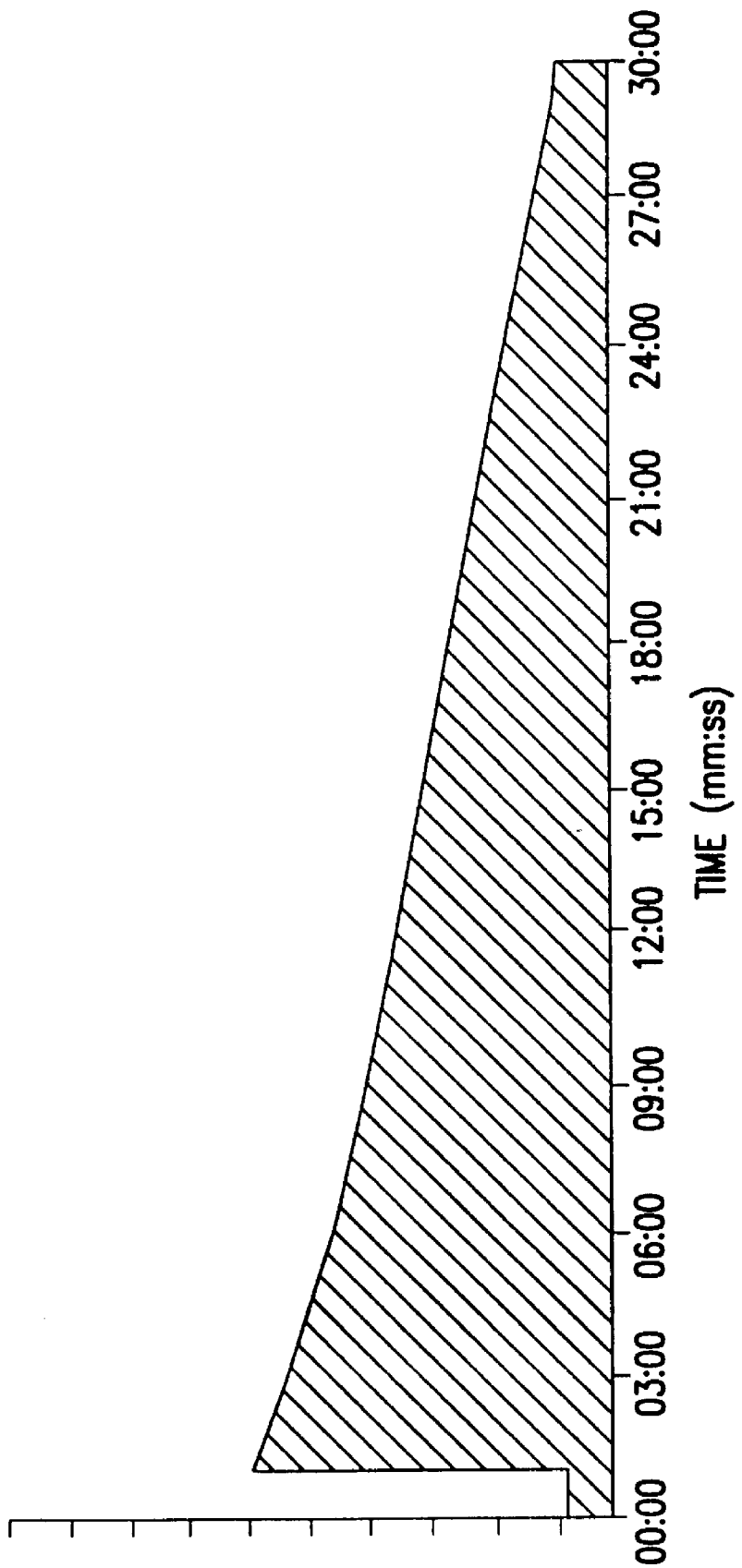

The novel chemiluminescent 3-(substituted adamant-2'-ylidene) 1,2-dioxetanes of this invention can be represented by the general formula:

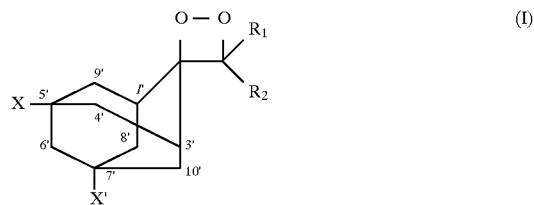

In Formula I, X and $X^1$ each represent, individually, a substituent at the 5' and 7' positions on the adamant-2'-ylidene substituent which can be hydrogen, a hydroxyl group (a slightly electron withdrawing group when hydrogen-bonded to water), a halo substituent, i.e., fluoro or chloro (electron withdrawing groups) or bromo or iodo (polarizable, mesomeric groups), an unsubstituted straight or branched chain lower alkyl group, preferably methyl; a substituted straight or branched chain lower alkyl group monosubstituted or having two or more substituents which can be the same or different, e.g., a hydroxyalkyl group such as a hydroxymethyl group, a haloalkyl group such as trifluoromethyl, and the like; an unsubstituted aryl group, preferably a phenyl group; a substituted aryl group, preferably one whose aryl ring contains six carbon atoms monosubstituted or having two or more substituents which can be the same or different, e.g., a halo substituent, as in p-bromophenyl or p-chlorophenyl, an alkoxy substituent, e.g., p-methoxyphenyl (an electron donating group), a hydroxyalkoxy substituent, e.g., hydroxyethoxy or hydroxypropoxy, a cyano group, or an amide group, e.g., a formamido or acetamido group, and the like, with the proviso that at least one of X and $X^1$ is other than hydrogen.

Also included within the scope of the novel chemiluminescent 3-(substituted adamant-2'-ylidene) 1,2-dioxetanes of this invention are compounds otherwise similar to those of Formula I above which, instead of bearing a substituent other than hydrogen at the 5' or 7', or 5' and 7' positions, are instead substituted at the 4' position with a methylene group.

When the adamantylidene group is monosubstituted with one of the foregoing substituents other than hydrogen, a mixture of the syn- and anti-isomers will be obtained when such compounds are synthesized. In certain cases, e.g., for monoiodo-substituted adamantylidene dioxetanes, one isomer will exhibit greater chemiluminescence intensity on decomposition than the other. In other cases, e.g., for monohydroxy-substituted adamantylidene dioxetanes, the two isomers will be equivalent or nearly so in chemiluminescence properties, such as intensity. In either case, the isomers may be separated before being used, e.g., as reporter molecules in bioassays, by techniques such as those disclosed in Edwards, et al. U.S. patent application Ser. No. 244,006, filed Sep. 14, 1988, or they may be used as chromatographed, isomeric mixtures without separation.

Dioxetanes whose adamantylidene substituents are further substituted with two of the foregoing substituents other than hydrogen (X and X'≠hydrogen) do not exhibit syn/anti isomerism, although, of course, position isomers are possible when two different substituents are present, e.g., 5'-hydroxy-7'-chloro- and 5'-chloro-7'-hydroxy-substituted adamantylidene dioxetanes.

The symbols $R_1$ and $R_2$ can represent any of the substituents on the 4-carbon atom of the dioxetane ring disclosed in the aforementioned Bronstein; Bronstein, et al.; Edwards; Edwards, et al. and Voyta, et al. applications, so long as when $R_1$ and $R_2$ represent individual substituents the $R_2$ substituent is aromatic, heteroaromatic, or an unsaturated substituent in conjugation with an aromatic ring, and at least one of $R_1$ and $R_2$ is, or $R_1$ and $R_2$ taken together are, an enzymatically cleavable labile group-substituted fluorescent chromophore group that produces a luminescent substance when the enzymatically removable labile substituent thereof is removed by an enzyme.

Thus, for example, the symbol $R_1$ can represent hydrogen, or a bond when $R_2$ represents a substituent bound to the dioxetane ring through a spiro linkage, or an organic substituent that does not interfere with the production of light and that satisfies the valence of the dioxetane ring carbon atom to which it is attached to result in a tetravalent dioxetane ring carbon atom, such as an alkyl, aryl, aralkyl, alkaryl, heteroalkyl, heteroaryl, cycloalkyl or cycloheteroalkyl group, e.g., a straight or branched chain alkyl group having from 1 to 7 carbon atoms, inclusive; a straight or branched chain hydroxyalkyl group having from 1 to 7 carbon atoms, inclusive, an —OR group in which R is a $C_1$–$C_{20}$ unbranched or branched, unsubstituted or substituted, saturated or unsaturated alkyl, cycloalkyl, cycloalkenyl, aryl, aralkyl or aralkenyl group, any of which may additionally be fused to $R_2$ such that the emitting fragment contains a lactone ring or an N, O or S heteroatom-containing group, or an enzyme cleavable group bonded directly to the 4-carbon atom of the dioxetane ring, or to one of the other aforementioned $R_1$ groups, that contains a bond cleavable by an enzyme to yield either directly or by subsequent adjustment of pH an electron-rich moiety, e.g., an oxygen anion, a sulfur anion or a nitrogen anion (the latter being, for example, an oxime or an amido anion such as a sulfonamido anion) bonded to the dioxetane ring. Preferably, $R_1$ is an alkoxy group, and especially a methoxy group, when $R_2$ is singly bonded to the dioxetane's 4-carbon atom.

The symbol $R_2$ can also represent any organic substituent that does not interfere with the production of light and that satisfies the valence of the 4-carbon atom of the dioxetane ring to which it is attached. Preferably, $R_2$ will represent any of a number of light-emitting fluorophore-forming fluorescent chromophore groups that permit the corresponding dioxetane decomposition fragments to absorb energy and form an excited state from which they emit optically detectable energy to return to their ground state, substituted with an enzyme cleavable group that contains a bond cleavable by an enzyme to yield either directly or by subsequent adjustment of pH an electron-rich moiety, again, for example, an oxygen anion, a sulfur anion or a nitrogen anion, bonded to the dioxetane ring.

Thus, for example, the symbol $R_2$ can represent, alone (or together with the symbol $R_1$ to give a substituent spiro bonded to the 4-carbon atom of the dioxetane ring) fluorescent chromophore groups such as:

phenyl and phenyl derivatives;

naphthalene and naphthalene derivatives e.g., 5-dimethylaminonaphthalene-1-sulfonic acid and hydroxy naphthalenes;

anthracene and anthracene derivatives, e.g., 9,10-diphenylanthracene, 9-methylanthracene, 9-anthracene carboxaldehyde, anthryl alcholols and 9-phenylanthracene;

rhodamine and rhodamine derivatives, e.g., rhodols, tetramethyl rhodamine, tetraethyl rhodamine, diphenyldimethyl rhodamine, diphenyldiethyl rhodamine and dinaphthyl rhodamine;

fluorescein and fluorescein derivatives, e.g., 5-iodoacetamido fluorescein, 6-iodoacetamido fluorescein and fluorescein-5-maleimide;

coumarin and coumarin derivatives, e.g., 7-dialkylamino-4-methylcoumarin, 4-bromomethyl-7-methoxycoumarin and 4-bromomethyl-7-hydroxy coumarin;

erythrosin and erythrosin derivatives, e.g., hydroxy eyrthrosins, erythrosin-5-iodoacetamide and erythrosin-5-maleimide;

acridine and acridine derivatives, e.g., hydroxy acridines and 9-methyl acridine;

pyrene and pyrene derivatives, e.g., N-(1-pyrene) iodoacetamide, hydroxy pryrenes and 1-pyrenemethyl iodoacetate;

stilbene and stilbene derivatives, e.g., 6,6'-dibromostilbene and hydroxy stilbenes;

nitrobenzoxadiazoles and nitrobenzoxadiazole derivatives, e.g., hydroxy nitrobenzoxadiazoles, 4-chloro-7-nitrobenz-2-oxa-1,3-diazole, 2-(7-nitrobenz-2-oxa-1,3-diazole-4-yl) methylaminoacetaldehyde and 6-(7'-nitrobenz-2-oxa-1,3-diazole-4-yl)aminohexanoic acid;

quinoline and quinoline derivatives, e.g., 6-hydroxyquinoline and 6-aminoguinoline;

acridine and acridine derivatives, e.g., N-methylacridine and N-phenylacridine;

acidoacridine and acidoacridine derivatives, e.g., 9-methylacidoacridine and hydroxy-9-methylacidoacridine;

carbazole and carbazole derivatives, e.g., N-methylcarbazole and hydroxy-N-methylcarbazole;

fluorescent cyanines, e.g., DCM (a laser dye), hydroxy cyanines, 1,6-diphenyl-1,3,5-hexatriene, 1-(4-dimethyl aminophenyl)-6-phenylhexatriene and the corresponding 1,3-butadienes;

carbocyanines and carbocyanine derivatives, e.g., phenylcarbocyanine and hydroxy carbocyanines;

pyridinium salts, e.g., 4(4-dialkyldiaminostyryl)-N-methyl pyridinium iodate and hydroxy-substituted pyridinium salts;

oxonols; and resorofins and hydroxy resorofins.

The symbol $R_2$, together with the symbol $R_1$, can also represent a fused fluorescent chromophore group, bonded to the 4-carbon atom of the dioxetane ring through a spiro linkage, having the general formula:

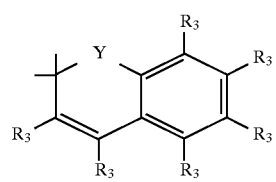

In this formula Y is

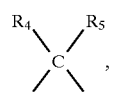

—O—, —S—, or —$NR_6$, where each of $R_4$, $R_5$ and $R_6$, independently, is hydrogen, a branched or straight chain alkyl group having 1 to 20 carbon atoms, inclusive, e.g., methyl, n-butyl or decyl, a branched or straight chain heteroalkyl group having 1 to 7 carbon atoms, inclusive, e.g., methoxy, hydroxyethyl or hydroxypropyl; an aryl group having 1 or 2 rings, e.g, phenyl, naphthyl or anthryl; a heteroaryl group having 1 or 2 rings, e.g., pyrrolyl or pyrazolyl; a cycloalkyl group having 3 to 7 carbon atoms, inclusive, in the ring, e.g., cyclohexyl; a heterocycloalkyl group having 3 to 6 carbon atoms, inclusive, in the ring, e.g., dioxane; an aralkyl group having 1 or 2 rings, e.g., benzyl; or an alkaryl group having 1 or 2 rings, e.g., tolyl; and each $R_3$, independently, can be hydrogen; an electron-withdrawing group, such as a perfluoroalkyl group having between 1 and 7 carbon atoms, inclusive, e.g., trifluoromethyl; a halogen; $CO_2H$, $-ZCO_2H$, $-SO_3H$, $ZSO_3H$, $-NO_2$, $-ZNO_2$, $-C\equiv N$, or $-Z_1C\equiv N$, where Z is a branched or straight chain alkyl group having 1 to 7 carbon atoms, inclusive, e.g., methyl; an aryl group having 1 or 2 rings, e.g., phenyl; an electron-donating group, e.g., a branched or straight chain $C_1$–$C_7$ alkoxy group, e.g., methoxy or ethoxy; an aralkoxy group having 1 or 2 rings, e.g., phenoxy; a branched or straight chain $C_1$–$C_7$ hydroxyalkyl group, e.g., hydroxymethyl or hydroxyethyl; a hydroxyaryl group having 1 or 2 rings, e.g., hydroxyphenyl; a branched or straight chain $C_1$–$C_7$ alkyl ester group, e.g., acetate; an aryl ester group having 1 or 2 rings, e.g., benzoate; or a heteroaryl group having 1 or 2 rings, e.g., benzoxazole, benzthiazole, benzimidazole or benztriazole. Furthermore, two or more of the $R_3$ groups can form a fused ring or rings which can themselves be unsubstituted or substituted.

The symbol $R_2$, alone or together with the symbol $R_1$, can likewise represent a particular class of fused polycyclic ring-containing fluorophore moieties having a labile ring substituent containing a bond which, when cleaved, renders the fused polycyclic moiety electron-rich to in turn render the dioxetane compound decomposable to emit light. The members of this class are those in which the labile ring substituent's point of attachment to the fused polycyclic ring, in relation to this ring's point(s) of attachment to the dioxetane ring (single bond attachment or, when $R_1$ represents a bond, a spiro linkage), is such that the total number of ring $sp^2$ atoms separating these points of attachment, including the $sp^2$ ring carbon atoms at the points of attachment, is an odd whole number; see the Edwards, et al. '672 application.

Included among the fused polycyclic ring compounds whose residues can be used to form this fluorophore moiety are the fused polycyclic aromatic hydrocarbon ring fluorophoric compounds mentioned above, and particularly ones containing from 9 to about 30 ring carbon atoms, inclusive, such as naphthalene:

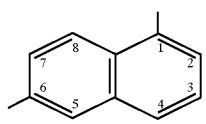

the substituent bonds indicating a 1,6-substitution pattern as in disodium 6-(4-methoxyspiro[1,2-dioxetane-3,2'-(5'-hydroxy)tricyclo[$3.3.1.1^{3,7}$]decan]-4-yl)-1-naphthalenyl phosphate, pentalene, azulene, heptalene, as-indacene, s-indacene, biphenylene, perylene, acenaphthylene, phenanthrene, anthracene, acephenanthrylene, aceanthrylene, triphenylene, pyrene, chrysene, naphthacene, and the like, as well as derivatives thereof substituted with one or more non-labile substituents such as those mentioned above as being represented by the symbols $R_3$, $R_4$ and $R_5$.

The fused polycyclic ring portion of such "odd pattern substituted" fluorophore moieties represented by $R_2$ alone or together with $R_1$ can also be the residues of nonaromatic, i.e., less than fully aromatic, fused polycyclic hydrocarbon ring fluorophoric compounds, having a labile ring substituent containing a bond which, when cleaved, renders the fused, less than fully aromatic polycyclic moiety electron-rich to in turn render the dioxetane compound decomposable to emit light, unsubstituted or substituted with one or more of the aforementioned non-labile substituents, and containing from 10 to about 30 ring carbon atoms, inclusive, such as fluorene, 3,4-dihydro-3,3-dimethylnaphthalene, dibenzosuberene, 9,10-dihydrophenanthrene, indene, indeno [1,2-a] indene, phenalene, fluoroanthrene, and the like.

Further, the fused polycyclic ring portion of fluorophore moieties represented by $R_2$ alone or together with $R_1$ can also be the residue of a fused polycyclic heteroaromatic or less than fully aromatic fused ring heterocyclic fluorophore-forming group, e.g., dibenzothiophene, dibenzofuran, 2,2-dimethyl-2H-chromene, xanthene, piperidine, quinoline, isoquinoline, phenanthridine, carbostyryl, phenoxazine, phenothiazine, phenanthroline, purine, phthalazine, naphthyridine, N-acylindole, chroman, isochroman, N-acylindoline, isoindoline, and the like, unsubstituted or substituted with one or more of the aforementioned non-labile substituents, and containing from 9 to about 30 ring atoms, inclusive, the bulk of which are carbon atoms.

A preferred enzymatically removable group with which at least one of $R_1$ and $R_2$ is substituted is a phosphate group, particularly a phosphate ester group represented by the general formula:

(III)

wherein M+ represents a cation such as alkali metal, e.g., sodium or potassium, ammonium, or a $C_1$–$C_7$ alkyl, aralkyl or aromatic quaternary ammonium cation, $N(R_7)+_4$, in which each $R_7$ can be alkyl, e.g., methyl or ethyl, aralkyl, e.g., benzyl, or form part of a heterocyclic ring system, e.g., pyridinium. The disodium salt is particularly preferred. Such phosphate ester groups can be cleaved using an enzyme such as alkaline phosphatase to produce oxygen anion-substituted groups that will, in turn, destabilize the dioxetane with rupture of its oxygen-oxygen bond to produce light. The quaternary ammonium cations in such phosphate ester groups can also be connected through one of their guaternizing groups to a polymeric backbone, viz.

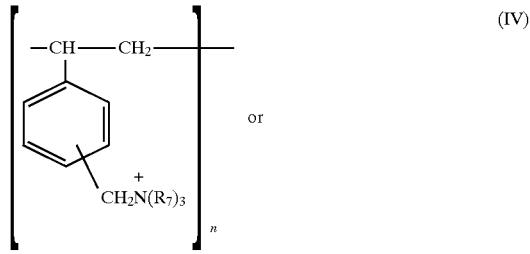

(IV)

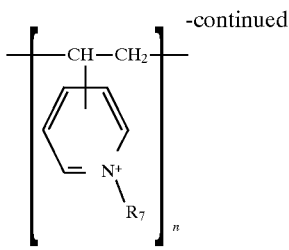

where n is greater than 1, or can be part of a polyquaternary ammonium salt, i.e., an ionene polymer.

Another preferred enzymatically removable group is the β-D-galactoside group, which can be cleaved with the enzyme β-D-galactosidase to yield the conjugate acid of the dioxetane phenolate, which upon pH adjustment chemiluminesces.

Enzymatically cleavable substituents that can be used also include enzyme-cleavable alkanoyloxy groups, e.g., an acetate ester group, or an enzyme-cleavable oxacarboxylate group, 1-phospho-2,3-diacylglyceride group, 1-thio-D-glucoside group, adenosine triphosphate analog group, adenosine diphosphate analog group, adenosine monophosphate analog group, adenosine analog group, α-D-galactoside group, β-D-galactoside group, α-D-glucoside group, β-D-glucoside group, α-D-mannoside group, β-D-mannoside group, β-D-fructofuranoside group, β-D-glucosiduronate group, p-toluenesulfonyl-L-arginine ester group or p-toluenesulfonyl-L-arginine amide group.

The substituted adamant-2-ylidene moiety spiro bonded to the 3-carbon atom of the dioxetane ring, illustrated in formula I above, can be replaced by other similarly substituted fused polycycloalkylidene groups having two or more fused rings, each ring having from 3 to 12 carbon atoms, inclusive, such as bicyclo[3.3.1.]nonan-9-ylidene, hexacyclo-[5.5.1.0.$^{2,6}$0.$^{3,10}$0.$^{4,8}$0$^{9,13}$]tridecan-5-ylidene, pentacyclo[5.4.0.0.$^{2,6}$0.$^{3,10}$0$^{5,9}$]undecan-4-ylidene, and the like.

PCT Application No. WO88/00695, published Jan. 28, 1988 based on the Bronstein '823 application, discloses enzymatically cleavable 1,2-dioxetanes which are substituted at the 3-carbon atom with a defined substituent "T-V" and at the 4-carbon atom with defined substituents "X" and "Y-Z". This published application also discloses, at p.3, 1s.6–12, that:

In preferred embodiments, one or more of groups T, X, or Y further include a solubilizing substituent, e.g., carboxylic acid, sulfonic acid, or quaternary amino salt; group T of the dioxetane is a polycycloalkyl group, preferably adamantyl; the enzyme-cleavable group includes phosphate; and the enzyme possesses phosphatase activity, at p.22,1.33–p.23,1.6 that:

For example, the enzyme-cleavable group Z can be bonded to group X of the dioxetane, instead of group Y. The specific affinity substance can be bonded to the dioxetane through groups X, Y, or T (preferably group X), instead of the enzyme. In this case, the group to which the specific affinity substance is bonded is provided with, e.g., a carboxylic acid, amino or maleimide substituent to facilitate bonding, and at p.23,1s.11–21 that:

Groups X, Y, or T of the dioxetane can be bonded to a polymerizable group, e.g., a vinyl group, which can be polymerized to form a homopolymer or copolymer.

Groups X, Y, or T of the dioxetane can be bonded to, e.g., membranes, films, beads, or polymers for use in immuno- or nucleic acid assays. The groups are provided with, e.g., carboxylic acid, amino, or maleimide substituents to facilitate bonding.

Groups X, Y, or T of the dioxetane can contain substituents which enhance the kinetics of the dioxetane enzymatic degradation, e.g., electron-rich moieties (e.g., methoxy).

Groups Y and T of the dioxetane, as well as group X, can contain solubilizing substituents.

The problem solved by the 3-(substituted adamant-2'-ylidene) 1,2-dioxetane compounds disclosed and claimed herein is not addressed in this published PCT application, nor are these compounds themselves disclosed in this or any other reference of which the inventors are aware.

The overall synthesis of these 3-(substituted adamant-2'-ylidene)-1,2-dioxetanes can be accomplished using methods such as those disclosed in the aforementioned Bronstein and Edwards applications and in Edwards, et al. U.S. patent application Ser. No. 279,176 ("'176 application"), filed Sep. 6, 1989. Thus, for example, 1,2-dioxetanes coming within the scope of formula I above in which X represents a hydroxyl group, $X^1$ represents hydrogen, $R_1$ represents a methoxy group and $R_2$ represents a phosphoryloxy salt-substituted phenyl group, preferably a meta-phosphoryloxy salt-substituted phenyl group, can be synthesized in accordance with the methods disclosed in the '176 application by a reaction sequence that can be illustrated schematically as follows:

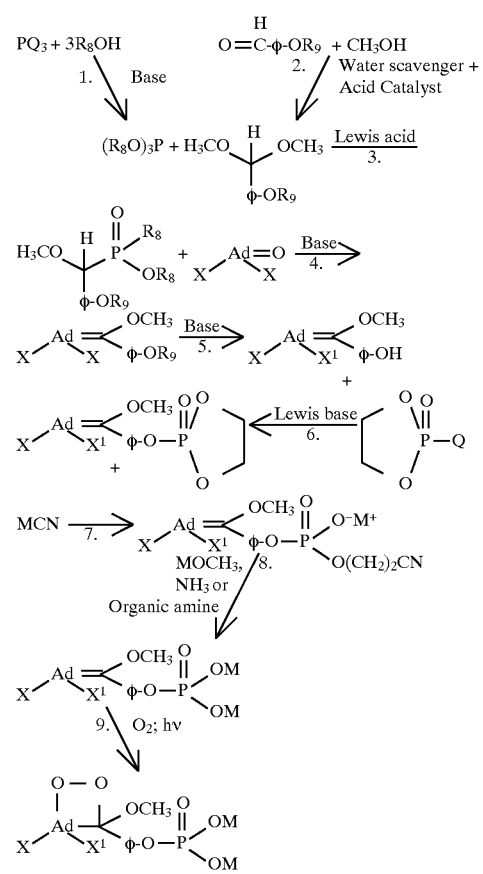

As specifically exemplified below, the

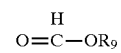

starting material can, if desired, be reacted with an orthoformate such as trimethylorthoformate, methanol, and p-toluenesulfonic acid, to give the intermediate:

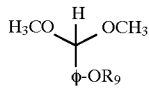

which, when then reacted with $(R_8O)_3P$ and Lewis acid, gives the phosphonate ester intermediate:

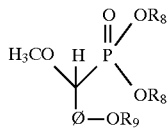

In the foregoing reaction sequence $R_8$ represents a lower alkyl group, e.g., methyl, ethyl or butyl. $R_9$ represents an acyl group containing from 2 to about 14 carbon atoms, inclusive, such as acetyl, propionyl, mesitoyl or pivaloyl, Q represents a halogen, e.g., chloro or bromo, or $OR_8$, and M represents, independently, a proton, a metal cation, e.g., $Na^+$, or $K^+$, or an ammonium, substituted ammonium, quaternary ammonium or $(H^+)$ pyridinium cation. Thiolate cleavage as described in the Edwards '197 application can be used in place of base cleavage of the $OR_9$ group in step 5 of the reaction sequence illustrated above, in which case $R_9$ can be a lower alkyl, lower alkenyl or aralkyl group, e.g., methyl, allyl or benzyl. The product of base or thiolate cleavage can have, in place of $R_9$, hydrogen or an alkali metal cation, e.g., lithium, sodium or potassium; see copending Edwards, et al. U.S. patent application Ser. No. 07/574,789, filed of even date herewith.

The intermediates represented above by the formula:

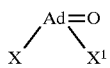

where only one of X and $X^1$ is other than hydrogen are known compounds, or are readily synthesizable from known starting materials using art-recognized methods. For example, in the case of the monosubstituted adamantan-2-ones (one of X and $X^1$ is hydrogen):

- 5-hydroxyadamantan-2-one is prepared as described in Geluk, *Synthesis*, 374 (1972);
- 5-bromoadamantan-2-one and 5-chloroadamantan-2-one are prepared as described in Geluk, et al., *Tetrahedron*, 24, 5369 (1968).

Where X or $X^1$ is fluoro, unsubstituted (lower) alkyl, e.g., t-butyl, substituted (lower) alkyl, e.g., trifluoromethyl, unsubstituted aryl, e.g., phenyl, or substituted aryl, e.g., p-chlorophenyl, p-methoxyphenyl or p-nitrophenyl, see le Noble, et al., *J. Am. Chem. Soc.*, 108 1598 (1986) and Walborsky, et al., *J. Am. Chem. Soc.*, 109, 6719 (1987) (X or $X^1$=hydroxymethyl).

Simple unit processes allow the conversion of several of the abovementioned X or $X^1$ substituents, or others known in the art, to 5-X- or 5-$X^1$-adamantane-2-ones where X or $X^1$ may be trialkylsilyloxy, iodo or cyano groups. These moieties are stable under the mild conditions used in step 4 of the foregoing reaction sequence. For example, when 5-hydroxyadamantan-2-one is refluxed for 7 hours with 57% hydriodic acid, 5-iodoadamantan-2-one (m.p. 73°–76° C.) is obtained. 5-Carboxyadamantan-2-one, prepared as described in Lantvoev, *J.Obshch.Khim.*, 12, 2361 (1976) or Le Noble, et al., *J.Org.Chem.*, 48, 1101 (1983), after saponification of the methyl ester, can be converted to 5-cyanoadamantan-2-one by the three step procedure of Tabushi, et al., *J.Org.Chem.*, 38, 3447 (1973), used for access to the isomeric 1-cyanoadamantan-2-one through the intermediacy of a keto amide. 5-Trimethylsilyloxyadamantan-2-one (m.p. 34°–38° C.), useful as a protected version of 5-hydroxyadamantan-2-one, allows the use of only one equivalent of base in step 4 of the foregoing reaction sequence to prepare the corresponding enol ether, which can then be desilylated using standard techniques.

As will be appreciated by one skilled in the art, other X and $X^1$ groups need not be static during the entire reaction sequence, but may be transformed by reactions which are compatible with other structural considerations at any stage. For example, it has been discovered that when X or $X^1$ is a chlorine or a bromine atom, enol ether intermediates produced in steps 4 and 5 of the foregoing reaction sequence are subject to facile solvolysis in the presence of molar excesses of diols or liquid ammonia in a bomb at high temperature. The reaction rate with diols such as ethylene glycol or propylene glycol becomes appreciable only at elevated temperatures (105°–120° C.) in the presence of a proton acceptor such as potassium carbonate. In general, this reaction is slow, but clean, and avoids the use of silver or heavy metal salts often used to stimulate hydroxyalkyl ether formation. 3-(Methoxy-5-(2-hydroxyethoxy)tricyclo-[3.3.1.1$^{3,7}$]dec-2-ylidenemethyl)phenol can be esterified with trimethylacetyl chloride and triethylamine to give the corresponding diester, which can then be selectively cleaved, using potassium carbonate in methanol, to give the phenolic monoester. The ensuing phosphorylation step, incorporating simultaneous β-elimination and saponification of the hindered ester with sodium methoxide in methanol, will furnish the hydroxyethoxy enol ether phosphate.

Reaction with liquid ammonia in dioxane, under pressure, to give 3-(methoxy-5-aminotricyclo[3.3.1.1$^{3,7}$]dec-2-ylidenemethyl)phenol from the corresponding 5-bromo compound is carried out using the procedure described by Hummelen, Dissertation, University of Groningen, The Netherlands, p. 60 (1985). Immediate acylation of the thus-obtained amino enol ether phenol, using two equivalents of acetyl chloride or acetic formic anhydride and 4-dimethylaminopyridine as the base, following the procedure of Gawronski, et al., *J. Am. Chem. Soc.*, 109, 6726 (1987) used for the esterification of (5-hydroxyadamantylidene)ethanol, will give the formamido or acetamido phenolic esters, which can be selectively saponified as described supra and then phosphorylated and photooxygenated as described infra.

Meijer, Dissertation, University of Groningen, The Netherlands (1982); Numan, et al., *J.Org.Chem.*, 43, 2232 (1978); and Faulkner, et al., *J.Chem.Soc., Chem.Comm.*, 3906 (1971), provide access to 4-methyleneadamantan-2-one (X and $X^1$=hydrogen, methylene at the 4' position in Formula I above) as the starting material for step 4 of the foregoing reaction sequence and subsequent reaction with a suitable phosphonate-stabilized carbanion. The difference in the reactivity of singlet oxygen toward the enol ether instead of the exomethylene function ensures that disodium 3-(4-methoxyspiro-[1,2-dioxetane-3,2'-(4'-methylene)tricyclo [3.3.1.1$^{3,7}$]decan]-4-yl-)phenyl phosphate will be obtained as the photooxygenation product.

If a selectively cleavable pivaloyloxyaryl enol ether will be obtained in any of the reactions immediately preceding the addition of an enzyme-removable group such as a phosphate ester group, it will be more convenient to avoid isolation of the hydroxyaryl enol ether. This can be accomplished by directly splitting the pivaloyl ester with one equivalent of sodium methoxide in methanol and isolating the sodium aryloxide species as a dry solid by removing all volatiles at the conclusion of the reaction. In such a case, step 6 of the foregoing reaction sequence will be run using this preformed salt in a dry, polar aprotic solvent such as dimethylformamide without using a Lewis base, and the inorganic salt by-products will be removed in the work-up phase of step 7 or step 8.

The 2-cyanoethylphosphate diester product of step 7 undergoes beta-elimination to the phosphate monoester in step 8. In step 8, the derivatives where X or $X^1$=chlorine or bromine are preferably reacted with a volatile amine such as ammonia, or with a solvent-soluble organic amine such as "DBU" (1,8-diazabicyclo[5.4.0]undec-7-ene) in an alcohol solvent, e.g., methanol. The use of ammonia at atmospheric pressure or above and at ambient temperatures is particularly advantageous, as excess base is simply volatized in vacuo at the end of the reaction.

Oxidation of the enol ether phosphate in step 9 of the foregoing reaction sequence can be carried out photochemically, as indicated, by reaction with singlet oxygen ($^1O_2$) in a halogenated solvent, e.g., a halogenated hydrocarbon such as chloroform, which may also contain a cosolvent, e.g., a lower alkanol such as methanol. Singlet oxygen can be generated using a photosensitizer such as polymer-bound Rose Bengal (Polysciences, Inc.), methylene blue, or 5, 10, 15, 20-tetraphenyl-21H, 23H-porphine ("TPP").

Alternatively, the crude 2-cyanoethyl phosphate diesters obtained in step 7 of the foregoing reaction sequence can be oxidized with singlet oxygen to their 1,2-dioxetane counterparts. Subsequent reaction with sodium methoxide in methanol at room temperature, followed by aqueous work-up and preparative reverse phase high pressure liquid chromatography, gives the pure 1,2-dioxetane phosphate monoester salts as mixtures of their syn- and anti-isomers. Chemical methods of 1,2-dioxetane formation, including ones using triethylsilylhydrotrioxide, phosphate ozonides or triarylamine radical cation-mediated one electron oxidation in the presence of triplet oxygen, can also be used.

Starting materials of the formula:

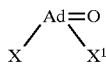

where both X and $X^1$ are the same and are other than hydrogen, or intermediates from which such starting materials can be synthesized using art-recognized methods, are also known. For example, the use of symmetrically substituted 5,7-bis-X,$X^1$-adamantan-2-ones in step 4 of the foregoing reaction sequence will result in symmetrical 1,2-dioxetanes which contain X and $X^1$ substituents in both a syn and anti relationship to the four-membered dioxetane ring. The quinone monoacetal-based synthesis strategy of Stetter, et al. provides access to 5,7-dihydroxyadamantan-2-one by way of bicyclo[3.3.1]nonan-3,7-dione-9-ethyleneacetal; Stetter, et al., *Liebigs Ann. Chem.*, 1807 (1977); see also Hamill, et al., *Tetrahedron*, 27, 4317 (1971). 5,7-Dihydroxyadamantan-2-one can be converted to 5,7-dibromoadamantan-2-one or its 5,7-dichloro and 5,7-diiodo analogs using 47% aqueous hydrobromic acid, thionyl chloride or 57% aqueous hydriodic acid under the conditions described in Geluk, et al., loc. cit. 5,7-Dialkyladamantan-2-ones, e.g., 5,7-dimethyl-adamantan-2-one, can be synthesized by the method of Kira, et al., *J. Am. Chem. Soc.*, 111, 8256 (1989). Solvolysis of 3-(methoxy-5,7-dibromotricyclo [3.3.3.1$^{3,7}$]dec-2-ylidenedimethyl)phenol with diols such as ethylene glycol or 1,4-butanediol in the presence of potassium carbonate will also furnish the corresponding symmetrical bis-hydroxyalkoxy-substituted 1,2-dioxetanes upon following the modified route to the mono-substituted derivatives described above.

When one wishes to take advantage of cooperative effects produced by an X group other than hydrogen that is different from an $X^1$ group also present that is also other than hydrogen, particularly where advantages can be obtained using such enzymatically cleavable 1,2-dioxetanes as isomeric mixtures, unsymmetrical 5,7(X,$X^1$)adamantan-2-ones will be used in step 4 of the foregoing reaction sequence. 5-Bromo-7-trifluoroadamantan-2-one can be prepared according to the method disclosed in Sorochinskii, et al., *Zh. Obshch. Khim.*, 17, 2339 (1981). 5-Chloro-7-hydroxyadamantan-2-one and 5-methyl-7-hydroxyadamantan-2-one have been described by Stetter, et al., loc. cit., and 5-bromo-7-hydroxyadamantan-2-one can be synthesized from 7-methylenebicyclo[3.3.1]nonane-3,9-dione-9-ethylene acetal following the procedure of Stetter, et al., by dissolving this compound in anhydrous ethanol and saturating the solution at 0° C. with gaseous hydrogen bromide instead of the gaseous hydrogen chloride used to obtain the corresponding chloro derivative.

Intermediates and methods for the synthesis of compounds of formula I above in which $R_1$ is other than lower alkoxy and $R_2$ is other than phosphoryloxy salt-substituted phenyl are found in the abovementioned Bronstein, Bronstein, et al., Edwards and Edwards, et al., ('672) applications.

This invention, as indicated above, is also directed to the use of its chemiluminescent, enzymatically cleavable substituted 1,2-dioxetanes in art-recognized assays, including assays for detecting enzymes in samples, to kits for use in such assays, and to like uses and means for accomplishing such uses.

For example, when using this invention to detect an enzyme in a sample, the sample is contacted with a dioxetane bearing a group capable of being cleaved by the enzyme being detected. The enzyme cleaves the dioxetane's enzyme cleavable group to form a negatively charged substituent (e.g., an oxygen anion) bonded to the dioxetane. This negatively charged substituent in turn destabilizes the dioxetane, causing the dioxetane to decompose to form a fluorescent chromophore group that emits light energy. It is this chromophore group that is detected as an indication of the presence of the enzyme. By measuring the intensity of luminescence, the concentration of the enzyme in the sample can also be determined.

A wide variety of other assays exist which use visually detectable means to determine the presence or concentration of a particular substance in a sample. The above-described dioxetanes can be used in any of these assays. Examples of such assays include immunoassays to detect antibodies or antigens, e.g., δ- or β-hCG; enzyme assays; chemical assays to detect, e.g., potassium or sodium ions; and nucleic acid assays to detect, e.g., viruses (e.g., HTLV III or cytomegalovirus, or bacteria (e.g., *E. coli*), and certain cell functions (e.g., receptor binding sites).

When the detectable substance is an antibody, antigen, or nucleic acid, the enzyme capable of cleaving the enzyme cleavable group of the dioxetane is preferably bonded to a substance having a specific affinity for the detectable substance (i.e., a substance that binds specifically to the detectable substance), e.g., an antigen, an antibody, or a nucleic acid probe. Conventional methods, e.g., carbodiimide coupling, are used to bond the enzyme to the specific affinity substance; bonding is preferably through an amide linkage.

In general, assays are performed as follows. A sample suspected of containing a detectable substance is contacted with a buffered solution containing an enzyme bonded to a substance having a specific affinity for the detectable substance. The resulting solution is incubated to allow the detectable substance to bind to the specific affinity portion of the specific affinity-enzyme compound. Excess specific affinity-enzyme compound is then washed away, and a dioxetane having a group cleavable by the enzyme portion of the specific affinity-enzyme compound is added. The enzyme cleaves the enzyme cleavable group, causing the dioxetane to decompose into two carbonyl compounds (e.g., an ester, a ketone or an aldehyde). The chromophore to which the enzyme cleavable group had been bonded is thus excited and luminesces. Luminescence is detected (using, e.g., a cuvette, or light-sensitive film in a camera luminometer, or a photoelectric cell or photomultiplier tube), as an indication of the presence of the detectable substance in the sample. Luminescence intensity is measured to determine the concentration of the substance.

Examples of specific assays follow.

A. Assay for Human IgG

A 96-well microtiter plate is coated with sheep anti-human IgG (F(ab)$_2$ fragment specific). A serum sample containing human IgG is then added to the wells, and the wells are incubated for 1 hour at room temperature.

Following the incubation period, the serum sample is removed from the wells, and the wells are washed four times with an aqueous buffer solution containing 0.15M NaCl, 0.01M phosphate, and 0.1% bovine serum albumin (pH 7.4).

Alkaline phosphatase bonded to anti-human IgG is added to each well, and the wells are incubated for 1 hr. The wells are then washed four times with the above buffer solution, and a buffer solution of a phosphate-containing dioxetane of this invention is added. The resulting luminescence caused by enzymatic degradation of the dioxetane is detected in a luminometer, or with photographic film in a camera luminometer.

B. Assay for hCG

Rabbit anti-α-hCG is adsorbed onto a nylon-mesh membrane. A sample solution containing hCG, e.g., urine from a pregnant woman, is blotted through the membrane, after which the membrane is washed with 1 ml of a buffer solution containing 0.15M NaCl, 0.01M phosphate, and 0.1% bovine serum albumin (pH 7.4).

Alkaline phosphatase-labeled anti-β-hCG is added to the membrane, and the membrane is washed again with 2 ml of the above buffer solution. The membrane is then placed in the cuvette of a luminometer or into a camera luminometer, and contacted with a phosphate-containing dioxetane of this invention. The luminescence resulting from enzymatic degradation of the dioxetane is then detected.

C. Assay for Serum Alkaline Phosphatase 2.7 ml of an aqueous buffer solution containing 0.8M 2-methyl-2-aminopropanol is placed in a 12×75 mm pyrex test tube, and 0.1 ml of a serum sample containing alkaline phosphatase added. The solution is then equilibrated to 30° C. 0.2 ml of a phosphate-containing dioxetane of this invention is added, and the test tube immediately placed in a luminometer to record the resulting luminescence. The level of light emission will be proportional to the rate of alkaline phosphatase activity.

D. Nucleic Acid Hybridization Assay

A sample of cerebrospinal fluid (CSF) suspected of containing cytomegalovirus is collected and placed on a membrane, e.g., a nylon or nitrocellulose membrane. The sample is then chemically treated with urea or guanidinium isothiocyanate to break the cell walls and the degrade all cellular components except the viral DNA. The strands of the viral DNA thus produced are separated and attached to the nitrocellulose filter. A DNA probe specific to the viral DNA and labeled with alkaline phosphatase is then applied to the filter; the probe hybridizes with the complementary viral DNA strands. After hybridization, the filter is washed with an aqueous buffer solution containing 0.2M NaCl and 0.1 mM Tris-HCl (pH=8.10) to remove excess probe molecules. A phosphate-containing dioxetane of this invention is added and the resulting luminescence from the enzymatic degradation of the dioxetane is measured in a luminometer or detected with photographic film.

E. Assay for Galactosidase

In the assays described above and in the working examples to follow dioxetanes containing α- or β-galactosidase-cleavable α-D- or β-D-galactoside (galactopyranoside) groups, respectively, can be added, and the luminescence resulting from the enzymatic cleavage of the sugar moiety from the chromophore measured in a luminometer or detected with photographic film.

F. Electrophoresis

Electrophoresis allows one to separate complex mixtures of proteins and nucleic acids according to their molecular size and structure on gel supports in an electrical field. This technique is also applicable to separate fragments of protein after proteolysis, or fragments of nucleic acids after scission by restriction endonucleases (as in DNA sequencing). After electrophoretic resolution of species in the gel, or after transfer of the separated species from a gel to a membrane, the bonds are probed with an enzyme bound to a ligand. For example, peptide fragments are probed with an antibody covalently linked to alkaline phosphatase. For another example, in DNA sequencing alkaline phosphatase—avidin binds to a biotinylated nucleotide base. Thereafter, an AMPPD analog of this invention is added to the gel or membrane filter. After short incubation, light is emitted as the result of enzymatic activation of the dioxetane to form the emitting species. The luminescence is detected by either X-ray or instant photographic film, or scanned by a luminometer. Multichannel analysis further improves the process by allowing one to probe for more than one fragment simultaneously.

G. Solid State Assays

In solid state assays, it is desirable to block nonspecific binding to the matrix by pretreatment of nonspecific binding sites with nonspecific proteins such as bovine serum albumin (BSA) or gelatin. It has been found that some commercial preparations of BSA contain small amounts of substances that exhibit phosphatase activity that will produce undesirable background chemiluminescence from AMPPD. It has also been discovered, however, that certain water-soluble synthetic macromolecular substances are efficient blockers of nonspecific binding in solid state assays using dioxetanes. Preferred among such substances are water-soluble polymeric quaternary ammonium salts such as BDMQ, poly(vinylbenzyltrimethylammonium chloride) (TMQ), and poly(vinylbenzyltributylammonium chloride) (TBQ). Other such substances are disclosed in the aforementioned Voyta, et al. '263 application and listed in Table III below.

H. Assay for Nucleotidase

An assay for the enzyme ATPase is performed in two steps. In the first step, the enzyme is reacted at its optimal pH (typically pH 7.4) with a substrate comprising ATP covalently linked via a terminal phosphoester bond to a chromophore-substituted 1,2-dioxetane to produce a phosphoryl-chromophore-substituted 1,2-dioxetane. In the second step, the product of the first step is decomposed by the addition of acid to bring the pH to below 6, preferably to pH 2–4, and the resulting light measured in a luminometer or detected with chromatographic film. In a similar two-step procedure, ADPase is assayed using as the substrate an ADP derivative of a chromophore-substituted 1,2-dioxetane of this invention, and 5'-nucleotidase assayed using as the substrate an adenylic acid derivative of a chromophore-substituted 1,2-dioxetane of this invention. The second step can also be carried out by adding the enzyme alkaline phosphatase to decompose the phosphoryl-chromophore-substituted 1,2-dioxetane.

I. Nucleic Acid Sequencing

DNA or RNA fragments, produced in sequencing protocols, can be detected after electrophoretic separation using the chemiluminescent 1,2-dioxetanes of this invention.

DNA sequencing can be performed by a dideoxy chain termination method [Sanger, F., et al., *Proc. Nat. Acad. Sci. (USA)*, 74:5463 (1977)]. Briefly, for each of the four sequencing reactions, single-stranded template DNA is mixed with dideoxynucleotides and biotinylated primer strand DNA. After annealing, Klenow enzyme and deoxyadenosine triphosphate are incubated with each of the four sequencing reaction mixtures, then chase deoxynucleotide triphosphate is added and the incubation continued.

Subsequently, DNA fragments in reaction mixtures are separated by polyacrylamide gel electrophoresis (PAGE). The fragments are transferred to a membrane, preferably a nylon membrane, and the fragments cross-linked to the membrane by exposure to UV light, preferably of short wave length.

After blocking non-specific binding sites with a polymer, e.g., heparin, casein or serum albumin, the DNA fragments on the membrane are contacted with avidin or streptavidin covalently linked to an enzyme specific for the enzyme-cleavable group of the particular 1,2-dioxetane substrate of this invention being used. As avidin or streptavidin bind avidly to biotin, biotinylated DNA fragments will now be tagged with an enzyme. For example, when the chemiluminscent substrate is disodium 3-(4-methoxyspiro[1,2-dioxetane-3,2'-(5'-chloro) tricyclo[3.3.1.1$^{3,7}$]decan]-4-yl) phenyl phosphate dioxetane salt (Cl-AMPPD), avidin or streptavidin will be conjugated to a phosphatase. Similarly, when the chemiluminescent substrate is disodium 3-(4-methoxyspiro[1,2-dioxetane-3,2'-(5'-chloro)tricyclo [3.3.1.1$^{3,7}$]decan]-4-yl)phenyl β-D-galactopyranose (Cl-AMPGD), avidin or streptavidin are conjugated with β-galactosidase.

Following generation of luminescence by contacting the complex of DNA fragment-biotin-avidin (or streptavidin)-enzyme with the appropriate 1,2-dioxetane at alkaline pH values, e.g., above about pH 8.5, DNA fragments are visualized on light-sensitive film, e.g., X-ray or instant film, or in a photoelectric luminometer instrument.

The detection method outlined above can also be applied to the genomic DNA sequencing protocol of Church et al. [Church, G. M., et al., *Proc. Nat. Acad. Sci. (USA)*, 81:1991 (1984)]. After transferring chemically cleaved and electrophoretically separated DNA[Maxam, A. M. et al., *Proc. Nat. Acad. Sci. (USA)*, 74:560 (1977)] to a membrane, preferably a nylon membrane, and cross-linking the ladders to the membrane by UV light, specific DNA sequences may be detected by sequential addition of: biotinylated oligonucleotides as hybridization probes; avidin or streptavidin covalently linked to an enzyme specific for an enzyme-cleavable chemiluminescent 1,2-dioxetane of this invention; and, the appropriate 1,2-dioxetane. Images of sequence ladders (produced by PAGE) may be obtained as described above.

Serial reprobing of sequence ladders can be accomplished by first stripping the hybridized probe and chemiluminescent material from a membrane by contacting the membrane with a heated solution of detergent, e.g., from about 0.5 to about 5% sodium dodecylsulfate (SDS) in water at from about 80° C. to about 90° C., cooling to from about 50° C. to about 70° C., hybridizing the now-naked DNA fragments with another biotinylated oligonucleotide probe to generate a different sequence, then generating an imaging chemiluminescence as described above.

Similar detection methods can be applied to RNA fragments generated by RNA sequencing methods.

In order that those skilled in the art can more fully understand this invention, the following examples are set forth. These examples are given solely for purposes of illustration, and should not be considered as expressing limitations unless so set forth in the appended claims. All parts and percentages are weight by volume, except TLC solvent mixtures, which are volume by volume, or unless otherwise stated.

The $^1$H NMR data given in certain of these examples for enol ether intermediates uses the prime symbol (') to designate aromatic protons, while non-primed numbers refer, in all cases, to substituent adamant-2'-ylidene ring positions, thus:

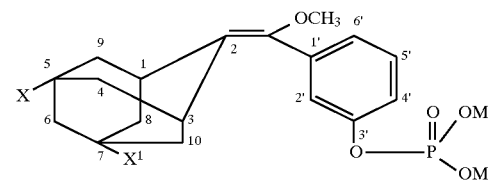

EXAMPLE I

Two hundred grams (1.64 mol) of 3-hydroxybenzaldehyde and 270 ml. (1.93 mol) of triethylamine were charged to a flask containing one liter of methylene chloride in an ice bath. The resulting brown solution was mechanically stirred, and 212 ml (1.72 mol) of trimethylacetyl chloride was added in a thin stream from an addition funnel over a 15 minute period. The resulting slurry was stirred for an additional 15 minutes, the ice bath was removed, and the reaction was then allowed to proceed for an additional two hours. TLC (K5F; 25% acetone-hexanes) showed the absence of starting material and a single higher R$_f$ product. The reaction mixture was transferred to a separatory funnel and admixed with 250 ml of 1M hydrochloric acid. The organic phase was then extracted with water (2×400 ml) and finally dried over sodium sulfate. The dried solution was passed through a silica gel plug, rotary evaporated, and then pumped under vacuum (1.0 mm Hg) to give 348 g of a greenish-brown oil: 3-pivaloyloxybenzaldehyde, which was held under an argon atmosphere.

EXAMPLE II

Four hundred mg of p-toluenesulfonic acid dissolved in 25 ml of methanol was added, with stirring, to the 3-pivaloyloxybenzaldehyde of Example I. Trimethylorthoformate (224 ml; 2.05 mol) was then added dropwise. The minor exotherm that resulted was allowed to proceed unchecked while the mixture was stirred for 1 hour. One half gram of sodium bicarbonate was added, and the flask was placed on the rotary evaporator (bath temperature 40° C.) to remove all volatiles. The resulting oil was passed through a short silica gel column under nitrogen pressure to give an orange-brown oil which was pumped under vacuum (1.0 mm Hg) with stirring to yield 426 g of crude 3-pivaloyloxybenzaldehyde dimethyl acetal. Infrared analysis revealed no aldehyde carbonyl absorption (1695 cm$^{-1}$).

EXAMPLE III

The crude 3-pivaloyloxybenzaldehyde dimethyl acetal of Example II was dissolved in one liter of methylene chloride, freshly distilled from $P_2O_5$, under an argon atmosphere in a 3 liter flask. Then, 347 ml (2.03 mol) of triethyl phosphite was added all at once. The flask was fitted with a septum inlet adapter and cooled in a dry ice-acetone bath under slight argon pressure. Boron trifluoride etherate (249 ml; 2.03 mol) was added in several portions by syringe, with vigorous stirring. The resulting reaction mixture was stirred at −55° C. for two hours, then stored in a freezer at −20° C. overnight.

Next, the flask was warmed to room temperature and its contents stirred for 4 hours. The orange-brown solution was then poured carefully into a vigorously stirred slurry of 170 g of sodium bicarbonate in 800 ml of water at a rate such that vigorous foaming was avoided. After vigorously stirring the biphasic mixture for one hour the layers were then separated in a separatory funnel and the aqueous layer was again extracted with methylene chloride (2×250 ml). The combined organic extracts were dried over sodium sulfate, concentrated, and vacuum distilled to yield 535 g of diethyl 1-methoxy-1-(3-pivaloyloxyphenyl)methane phosphonate as a clear, light yellow oil (b.p. 158°–161° C. at 0.25 mm Hg). This represented a 91% yield for the overall procedure of Examples I–III.

$^1$HNMR (400 MHz; CDCC$_3$): δ1.21 and 1.25 (6H, two t, 7 Hz, OCH$_2$C$\underline{H}_3$); 3.37 (3H, s, ArCHOC$\underline{H}_3$); 3.80 (3H, s, ArOC$\underline{H}_3$); 3.90–4.10 (4H, m, OC$\underline{H}_2$CH$_3$); 4.46 (1H, d, 15.6 Hz, ArC$\underline{H}$PO); 6.85 (1H, m); 7.00 (2H, m); 7.26 (1H, m).

IR (neat): 2974, 1596, 1582, 1480, 1255 (P=O), 1098, 1050, 1020, 965 cm$^{-1}$.

EXAMPLE IV

A solution of diisopropylamine (11.6 ml, 82.8 mmol) in 75 ml of tetrahydrofuran was cooled to −78° C. in a dry ice—acetone bath under an argon atmosphere. Thirty ml of a 2.5M solution of n-butyllithium in hexanes (Aldrich, 75.0 mmol) was added by syringe and, after stirring the resulting lithium diisopropylamide solution for 20 minutes, 13.47 g (37.6 mmol) of diethyl 1-methoxy-1-(3-pivaloyloxyphenyl) methane phosphonate in 25 ml of tetrahydrofuran was added dropwise from an addition funnel over a 5 minute period. The resulting red solution was stirred at low temperature for another 30 minutes to ensure complete formation of the phosphonate carbanion.

A solution of 4.99 g (30.1 mmol) of 5-hydroxyadamantan-2-one in 25 ml of tetrahydrofuran was then added dropwise. The resulting slightly cloudy mixture was stirred for 5 minutes at −78° C. and then slowly warmed to room temperature over 40 minutes. The solution, now orange in color, was refluxed for 90 minutes, cooled, diluted with 200 ml of a saturated sodium bicarbonate solution, and extracted with ethyl acetate (3×75 ml). The combined organic extracts were washed with a saturated sodium chloride solution, quickly dried over sodium sulfate and concentrated to give 12.49 g of an orange gum, a mixture of phenolic enol ether and its pivaloate ester.

$^1$HNMR (Pivaloate ester, 400 MHz, in CDCl$_3$): δ7.33 (1H, m, H-5'), 7.12 (1H, d, J=7.7 Hz, ArH), 6.95–7.02 (2H, m, ArH), 3.43 (1H, br. 8, H-1), 3.28 (3H, s, OMe), 2.79 (1H, br. s, H-3), 2.23 (1H, br. s, H-7), 1.59–1.87 (11H, m), 1.34 (9H, s, COC(CH$_3$)$_3$).

IR (in CHCl$_3$): 3590, 3442 (OH), 2924, 2848, 1742 (ester C=O), 1665, 1602, 1578, 1426, 1274, 1152, 1118, 918 cm$^{-1}$.

This mixture was taken up in 100 ml of methanol and refluxed for 3.5 hours in the presence of 10.7 g of anhydrous potassium carbonate. The methanol was then stripped off and the residue partitioned between water and ethyl acetate. The organic layer was washed with a saturated sodium chloride solution and rotary evaporated to a residue which was recrystallized from chloroform-petroleum ether to give 6.5 g of 3-(methoxy-5-hydroxytricyclo[3.3.1.1$^{3,7}$]dec-2-ylidenemethyl)phenol as an off-white solid (m.p. 171°–172° C.). An additional 0.80 g was obtained from the mother liquor, giving an overall yield of phenolic enol ether of 79%, based on 5-hydroxyadamantan-2-one.

$^1$HNMR (400 MHz, in CDCl$_3$): δ7.18 (1H, dd, J=8.4, 7.7 Hz, H-5'), 6.75–6.88 (3H, m, ArH), 6.36 (1H, br. s, ArOH), 3.41 (1H, br. s, H-1), 3.28 (3H, s, OMe), 2.79 (1H, br. s, H-3), 2.22 (1H, br. s, H-7), 1.56–1.98 (11H, m).

IR (in CHCl$_3$): 3586, 3320 (OH), 3000, 2920, 2844, 1665, 1590, 1578, 1445, 1296, 1092, 885 cm$^{-1}$.

HRMS calc. for $C_{18}H_{22}O_3(M^+)$ 286.1573, found 286.1569.

EXAMPLE V

A solution of 5.04 g (17.6 mmol) of 3-(methoxy-5-hydroxytricyclo[3.3.1.1$^{3,7}$]dec-2-ylidenemethyl)phenol in 35 ml of tetrahydrofuran, prepared under argon, was admixed with 3.4 ml (24.6 mmol) of triethylamine and then cooled to 0° C. in an ice bath. 2-Chloro-2-oxo-1,3,2-dioxaphospholane (1.95 ml, 21.1 mmol) was added dropwise with stirring. After 5 minutes the ice bath was removed, and stirring was continued for 45 minutes at room temperature. The reaction mixture was diluted with 30 ml of anhydrous diethyl ether and filtered under argon to exclude moisture. The triethylamine hydrochloride was then washed further with 20 ml of diethyl ether and the filtrate concentrated on the rotary evaporator to give the phosphate triester as a viscous, light orange oil.

The triester, dissolved in 30 ml of molecular sieve-dried dimethylformamide under argon, was reacted for 3.5 hours at room temperature with 1.02 g (20.8 mmol) of dry sodium cyanide, added all at once with stirring. The solvent was then removed under vacuum (1.0 mm Hg) with heating to 50° C. A sample of the resulting orange-brown residue, when dissolved in water and subjected to reverse phase analytical chromatography [0.1% sodium bicarbonate (water)—acetonitrile gradient] on a PLRP polystyrene column (Polymer Laboratories), evidenced complete reaction to the intermediate cyanoethyl phosphate diester sodium salt.

The residue was then taken up in 35 ml of methanol and treated dropwise with 4.85 ml of a 4.37M solution (21.2 mmol) of sodium methoxide in methanol, with stirring, for 30 minutes at room temperature. Reverse phase analytical HPLC showed β-elimination to the phosphate monoester to be complete. The solvent was removed and the residue triturated with 10% water/acetone to give a gummy solid. Further trituration with 3% water/acetone gave a hard, off-white solid which was filtered and dried under vacuum (1.0 mm Hg) to give 8.35 g of crude disodium 3-(methoxy-5-hydroxytricyclo[3.3.1.1$^{3,7}$]dec-2-ylidenemethyl) phenyl phosphate, contaminated with inorganic salts.

Reverse phase preparative HPLC using a water-acetonitrile gradient on a PLRP polystyrene column (Polymer Laboratories) and lyophilization of the appropriate fractions gave 5.2 g (72%) of purified compound as a white, granular solid, softening at 120° C. and melting to a light brown gum at 163°–168° C.

¹HNMR (400 MHz, in $D_2O$): δ7.16 (1H, dd, J=8.3, 7.4 Hz, H-5'), 7.05 (1H, d, J=8.3 Hz, ArH), 6.93 (1H, br. s, H-2'), 6.86 (1H, d, J=7.4 Hz, ArH), 3.2 (3H, s, OMe), 3.17 (1 H, br. s, H-1), 2.61 (1H, br. s, H-3), 2.06 (1H, br. s, H-7) 1.42–1.73 (10H, m).

Elemental analysis showed that the phosphate salt exists as a dihydrate. Anal. Calc. for $C_{18}H_{21}Na_2O_6P\cdot2H_2O$:C, 48.44, H, 5.65, P, 6.94. Found: C, 48.37, H, 5.90, P, 6.87.

EXAMPLE VI

A solution of 0.8 g of disodium 3-(methoxy-5-hydroxytricyclo [3.3.1.1³,⁷]dec-2-ylidenemethyl) phenyl phosphate in 96 ml of 25% anhydrous methanol/chloroform containing 5.35×10⁻⁵M methylene blue sensitizing dye was divided among three glass tubes. Each tube was then cooled to 5° C. in a water bath and saturated with oxygen by passing a stream of the gas through the solution. After 5 minutes, and while continuing to bubble oxygen through the solution, the tubes were irradiated with light from a cooled, 250 watt high pressure sodium vapor lamp while maintaining the temperature at 5° C. A 5 mil thick piece of Kapton polyimide film (duPont), placed between the sodium vapor lamp and the tubes, filtered out unwanted UV radiation. After 20 minutes of irradiation the solutions had turned pink. Reverse phase analytical HPLC [0.1% sodium bicarbonate (water)—acetonitrile gradient] on a PLRP polystyrene column (Polymer Laboratories) showed two product peaks: an early eluting, broadened peak (retention time=3.79 minutes) and a sharp, later eluting peak (retention time=5.77 minutes). The ratio of early eluting product (A) to later eluting product (B) was 1.3:1 in each tube's solution.

The solutions were combined and the solvent removed under vacuum (25.0 mm Hg) on an ice bath. The residue was then dissolved in 70 ml of water and filtered through a 0.45 µm nylon membrane. Reverse phase preparative HPLC (water-acetonitrile gradient) easily separated two products.

Combination of the appropriate preparative HPLC fractions, followed by analytical HPLC, showed them to be homogeneous. Lyophilization gave 0.32 g of one product (A) and 0.26 g of another (B), which were shown by ¹HNMR to be isomeric (syn and anti) 1,2-dioxetanes, i.e., syn-disodium 3-(4-methoxyspiro-[1,2-dioxetane-3,2'-(5'-hydroxy)tricyclo-[3.3.1.1³,⁷]decan]-4-yl)phenyl phosphate:

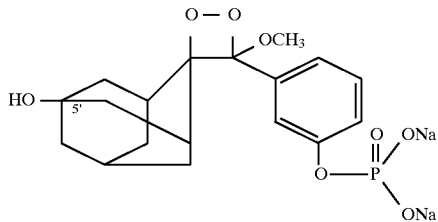

and its anti-isomer (anti-disodium 3-(4-methoxyspiro-[1,2-dioxetane-3,2'-(5'-hydroxy)tricyclo[3.3.1.1³,⁷]decan]-4-yl) phenyl phosphate):

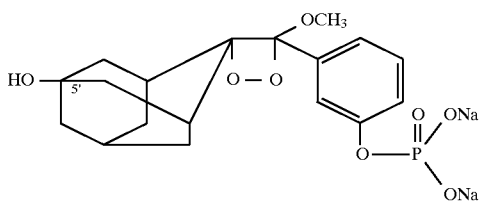

Each of these isomers produced chemiluminescence, with unique light vs. time and noise profiles, upon cleavage at pH 10 in aqueous buffer medium with alkaline phosphatase.

¹HNMR (A isomer, 400 MHz, in $D_2O$): δ6.98–7.6 (4H, m, ArH), 3.11 (3H, s, OMe), 2.97 (1H, br. s, H-1), 2.34 (1H, br. s, H-3), 1.79 (1H, br. s, H-7), 1.3–1.68 (8H, m), 1.01 (1H, d, J=13.5 Hz), 0.8 (1H, d, J=13 Hz).

¹HNMR (B isomer, 400 MHz, in $D_2O$): δ6.94–7.62 (4H, m, ArH), 3.09 (3H, s, OMe), 2.91 (1H, br. s, H-1), 2.27 (1H, br. s, H-3), 1.84 (1H, br. s, H-7), 1.21–1.75 (8H, m), 1.02 (1H, d, J=12.8 Hz), 0.87 (1H, d, J=12.8 Hz).

Elemental analysis showed that isomer B exists as a dihydrate. Anal. Calc. for $C_{18}H_{21}Na_2O_8P\cdot2H_2O$ (isomer B): C, 45.2, H, 5.27, P, 6.47. Found: C, 45.53, H, 5.35, P, 6.11.

It was not possible to specifically designate which of the two isomers obtained was the syn-isomer and which was the anti-isomer on the basis of ¹HNMR data.

EXAMPLE VII

Following in general the procedure of Example IV above, a solution of 5.35 ml (38.2 mmol) of diisopropylamine in 35 ml of tetrahydrofuran was cooled to –78° C. in an ice bath under an argon atmosphere. Fourteen ml of a 2.5M solution of n-butyllithium in hexanes (35.0 mmol) was added by syringe and, after stirring for 20 minutes, 10.86 g (30.3 mmol) of diethyl 1-methoxy-1-(3-pivaloyloxyphenyl) methane phosphonate in 30 ml of tetrahydrofuran was added dropwise over a 10 minute period. The resulting orange solution was stirred at low temperature for 1 hour, then admixed with a solution of 5.21 g (22.75 mmol) of 5-bromoadamantan-2-one in 20 ml of tetrahydrofuran over a 7 minute period, with stirring. Stirring was continued for an additional 10 minutes, at which point the cold bath was removed and the reaction mixture was allowed to warm slowly to room temperature over a one hour period.

The solution was then refluxed for another hour, cooled, diluted with 100 ml of hexanes, and poured into a separatory funnel containing saturated aqueous sodium bicarbonate solution and extracted with 10% ethyl acetate in hexanes (3×50 ml). The combined organic extracts were washed with an aqueous 15% sodium chloride solution, quickly dried over sodium sulfate, and concentrated to give 11.62 g of a light orange viscous oil. Plug filtration on a short silica gel column, eluting with 10% ethyl acetate in n-hexanes, gave 11.0 g of a yellowish-green gum.

¹HNMR (Pivaloyl ester, 400 MHz, in $CDCl_3$): δ7.34 (1H, t, J=7.8 Hz, H-5'), 7.1 (1H, d, J=7.7 Hz, ArH), 6.95–7.02 (2H, m, ArH), 3.39 (1H, br. s, H-1), 3.28 (3H, s, OMe), 2.74 (1H, br. s, H-3), 2.32–2.51 (6H, m, H-4, H-6, H-9), 2.17 (1H, br. s, H-7), 1.67–1.92 (4H, m, H-8, H-10), 1.34 (9H, s, $COC(CH_3)_3$).

IR (neat): 2924, 2850, 1745 (ester C=O), 1654, 1602, 1578, 1478, 1274, 1110, 1018, 808, 758 cm⁻¹.

This gum was taken up in 30 ml of methanol and refluxed for 2 hours with 2.4 g of anhydrous potassium carbonate. The methanol was then removed and the residue partitioned between water and 30% ethyl acetate in hexanes. The organic layer was washed with aqueous saturated sodium chloride solution, dried over sodium sulfate and concentrated to give 9.32 g of a yellow gum. This gum was flash chromatographed on silica gel to give 7.06 g (88% yield based on 5-bromoadamantan-2-one) of a slightly yellow gum that could not be crystallized. IR and NMR indicated, however, that the compound obtained, 3-(methoxy-5-bromotricyclo [3.3.1.1$^{3,7}$]dec-2-ylidenemethyl)phenol, was pure enough to be used for the ensuing phosphorylation reaction.

A sample of the pure phenolic compound was obtained from 3-(methoxy-5-bromotricyclo[3.3.1.1$^{3,7}$]dec-2-ylidenemethyl) phenyl acetate, obtained as follows: The impure phenolic compound (5.57 g; 15.95 mmol) was dissolved in 30 ml of molecular sieve-dried pyridine under an argon atmosphere. Fifty mg of 4-dimethylaminopyridine was added as catalyst. Next, 1.8 ml (19.15 mmol) of acetic anhydride was added by syringe and the reaction mixture was stirred at room temperature for 3 hours.

The reaction mixture was then transferred to a separatory funnel containing 250 ml of an aqueous saturated sodium bicarbonate solution, then extracted with 10% ethyl acetate in hexanes (2×100 ml). The combined extracts were washed several times with water, then quickly dried over sodium sulfate. The dried solution was concentrated on a rotary evaporator, and the residue was recrystallized from n-hexanes containing a few drops of ethyl acetate. The thus-obtained off-white solid was again recrystallized to give 5.21 g (83.5% yield) of the acetate, m.p. 108°–110° C.

HRMS calc. for $C_{20}H_{23}BrO_3(M^+)$ 390.0833, found 390.0831.

$^1$HNMR (400 MHz, in CDCl$_3$): δ7.35 (1H, dd, J=8, 7.7 Hz, H-5'), 7.13 (1H, dd, J=7.7, 1 Hz, ArH), 7.03 (1H, dd, J=8, 1 Hz, ArH), 6.99 (1H, d, 1 Hz, H-2'), 3.39 (1H, br. s, H-1), 3.27 (3H, s, OMe), 2.75 (1H, br. s, H-3), 2.32–2.51 (6H, m, H-4, H-6, H-9), 2.29 (3H, s, OAc), 2.18 (1H, br. s, H-7), 1.69–1.92 (4H, m, H-8, H-10).

IR (in CHCl$_3$): 3000, 2930, 2850, 1760 (ester C=O), 1660, 1602, 1577, 1368, 1192, 1095, 1070, 1016, 804 cm$^{-1}$.

Treatment of the recrystallized acetate with potassium carbonate in methanol for 15 hours at room temperature gave 3-(methoxy-5-bromotricyclo[3.3.1.1$^{3,7}$]dec-2-ylidenemethyl]phenol, m.p. 42°–45° C., as a white, crispy foam that could not be recrystallized further.

$^1$HNMR (400 MHz, in CDCl$_3$): δ7.21 (1H, t, J=7.2 Hz, H-5'), 6.73–6.85 (3H, m, ArH), 5.18 (1H, s, ArOH), 3.38 (1H, br. s, H-1), 3.28 (3H, s, OMe), 2.74 (1H, br. s, H-3), 2.3–2.52 (6H, m, H-4, H-6, H-9), 2.17 (1H, br. s, H-7), 1.68–1.92 (4H, m, H-8, H-10).

IR (in CHCl$_3$): 3584, 3320 (OH), 2925, 2850, 1665, 1588, 1578, 1445, 1435, 1092, 1080, 1015, 880, 808 cm$^{-1}$.

EXAMPLE VIII

Again following in general the procedure of Example IV above, a solution of 2.97 ml (21.3 mmol) of diisopropylamine in 21 ml of tetrahydrofuran was cooled to −78° C. in a dry ice-acetone bath under an argon atmosphere, admixed with 8.5 ml of a 2.5M solution of n-butyllithium in hexanes (21.3 mmol), added dropwise by syringe, and stirred for 20 minutes. Diethyl 1-methoxy-1-(3-pivaloyloxyphenyl) methane phosphonate (7.26 g; 20.3 mmol) in 20 ml of tetrahydrofuran was then added dropwise by syringe over a 10 minute period, and the solution was stirred at low temperature for 1 hour.

A solution of 2.79 g (15.2 mmol) of 5-chloroadamantan-2-one in 15 ml of tetrahydrofuran was added over a 5 minute period and, after stirring at low temperature for 10 minutes, the cold bath was removed and the mixture warmed to room temperature. The mixture was then refluxed for 1.5 hours, cooled, diluted with 50 ml of n-hexanes, and poured into a separatory funnel containing 150 ml of an aqueous saturated sodium bicarbonate solution. Extraction with 5% ethyl acetate-n-hexanes was followed by drying the combined organic fractions, concentrating them and pumping them under vacuum (1.0 mm Hg) to yield a residue which, when chromatographed on silica gel, gave 5.15 g of the higher R$_f$ 3-(methoxy-5-chlorotricyclo[3.3.1.1$^{3,7}$]dec-2-ylidenemethyl)phenyl trimethylacetate as a colorless oil (structure confirmed by IR and NMR), and 0.865 g of a later-eluting material composed predominantly of the corresponding phenol. This latter fraction, when reacylated with pivaloyl chloride and triethylamine in methylene chloride (see Example I above), followed by chromatography, gave an additional 0.35 g of the pivaloyl ester (93% total yield based on 5-chloroadamantan-2-one).

$^1$HNMR (Pivaloyl ester, 400 MHz, in CDCl$_3$): δ7.36 (1H, t, J=7.8 Hz, H-5'), 7.13 (1H, d, J=7.7 Hz, ArH), 6.98–7.04 (2H, m, ArH), 3.45 (1H, br. s, H-1), 3.3 (3H, s, OMe), 2.8 (1H, br. s, H-3), 2.13–2.32 (7H, m, H-4, H-6, H-7, H-9), 1.65–1.9 (4H, m, H-8, H-10), 1.36 (9H, s, COC(CH$_3$)$_3$).

IR (neat): 2932, 2835, 1750 (ester C=O), 1664, 1602, 1578, 1478, 1274, 1112, 1022, 827, 758 cm$^{-1}$.

The combined pivaloyl ester fractions (5.5 g, 14.1 mmol) were taken up in 40 ml of methanol and refluxed with 5.37 g of anhydrous potassium carbonate for 40 minutes. The residue remaining after the methanol was stripped off was partitioned between water and 30% ethyl acetate-hexanes, and the organic fractions were concentrated and plug filtered on a short silica gel column to give 4.07 g (88% yield based on 5-chloroadamantan-2-one) of 3-(methoxy-5-chlorotricyclo[3.3.1.1$^{3,7}$]dec-2-ylidenemethyl) phenol as a crispy white foam which became slightly tacky upon exposure to air.

HRMS calc. for $C_{18}H_{21}ClO_2(M^+)$ 304.1227, found 304.1230.

$^1$HNMR (400 MHz, in CDCl$_3$): δ7.23 (1H, dd, J=7.7, 7.6 Hz, H-5'), 6.85 (1H, d, J=7.6 Hz, ArH), 6.77–6.83 (2H, m, ArH), 3.44 (1H, br. s, H-1), 3.31 (3H, s, OMe), 2.8 (1H, br. s, H-3), 2.1–2.31 (7H, m, H-4, H-6, H-7, H-9), 1.65–1.89 (4H, m, H-8, H-10).

IR (in CHCl$_3$): 3590, 3330 (OH), 2930, 2855, 1655, 1590, 1580, 1440, 1295, 1094, 1080, 1022, 880, 826 cm$^{-1}$.

EXAMPLE IX 3-(Methoxy-5-bromotricyclo[3.3.1.1$^{3,7}$]dec-2-ylidenemethyl)phenol (1.49 g, 4.26 mmol) was dissolved in 8.5 ml anhydrous ethylene glycol and then placed, together with 0.28 g of potassium carbonate, in a sealed glass tube. The tube was heated in an oil bath at 110° C. for seven hours. The contents of the tube were then concentrated in vacuo (1.0 mm Hg) with ) heating. The residue was partitioned between saturated sodium chloride solution and ethyl acetate. The organic fraction was then stripped and chromatographed on a short silica gel column to furnish 1.31 g (92% yield based on the phenol starting material) of 3-(methoxy-5-(2-hydroxy)ethoxytricyclo[3.3.1.1$^{3,7}$]dec-2-ylidenemethyl)phenol as an off-white foam.

$^1$HNMR (400 MHz CDCl$_3$): δ7.19 (1H, t, J=7.6 Hz, H-5'), 6.83 (1H, d, J=7.6 Hz, ArH), 6.73–6.80 (2H, m, ArH), 5.83 (1H, s, ArOH), 3.67 (2H, m, OCH$_2$ CH$_2$ OH), 3.51 (2H, t,

J=4.6 Hz, OC$\underline{H}_2$ CH$_2$OH), 3.44 (1H, br. s, H-1), 3.28 (3H, s, OMe), 2.81 (1H, br. s, H-3), 2.24 (1H, br. s, H-7), 1.55–1.90 (10H, m).

IR (CHCl$_3$): 3580, 3320 (OH), 2929, 2842, 1664, 1586, 1575, 1440, 1092, 1078, 885 cm$^{-1}$.

EXAMPLE X 3-(Methoxy-5-chlorotricyclo[3.3.1.1$^{3,7}$]dec-2-ylidenemethyl)phenol (1.23 g, 4.0 mmol) was phosphorylated in the manner described in Example V above with one exception—ammonia in methanol was used for β-elimination. The crude ammonium sodium salt obtained was triturated with acetone, then pumped in vacuo (1.0 mm Hg) to give 1.2 g of an off-white solid. Reverse phase analytical HPLC showed that the phosphorylated enol ether product thus obtained was pure enough for direct photooxygenation to the corresponding 1,2-dioxetane.

The 3-(methoxy-5-chlorotricyclo[3.3.1.1$^{3,7}$]dec-2-ylidenemethyl)phenyl phosphate salt (0.65 g) was dissolved in 100 ml of anhydrous 10% methanol/chloroform which also contained 5.35×10$^{-5}$M methylene blue as a sensitizing dye. The resulting solution was divided among three glass tubes and irradiated as described in Example VI above. Work-up, in this case, involved dissolution of the pumped residue in 70 ml of water containing 258 mg of sodium bicarbonate. Upon carrying out reverse phase preparative HPLC, the syn- and anti-isomers were collected together, excluding impurities. Analytical HPLC [0.1% NaHCO$_3$ (H$_2$O)-acetonitrile gradient] showed two product peaks (retention times of 8.01 and 8.32 minutes). The area percent ratio (270 nm) of the early eluting isomer to the later eluting isomer was found to be 0.4:1. $^1$H NMR confirmed that the lyophilized white solid obtained was a mixture of syn- and anti-disodium 3-(4-methoxyspiro-[1,2-dioxetane-3,2'-(5'-chloro)tricyclo[3.3.1.1$^{3,7}$]decan]-4-yl)phenyl phosphate.

Elemental analysis indicated that the product exists in the form of a dihydrate. Anal. Calc. for C$_{18}$H$_{20}$ClNa$_2$O$_7$P.2H$_2$O: C, 43.52; H, 4.87; Cl, 7.14. Found:C, 43.23; H, 4.99; Cl, 7.65.

$^1$HNMR(400 MHz, in D$_2$O, two isomers): δ6.97–7.68 (4H, m, ArH), 3.08 and 3.09 (3H, 2s, OMe), 2.95 (1H, br.s, H-1), 0.76–2.35 (12H, m).

EXAMPLE XI 3-(Methoxy-5-bromotricyclo[3.3.1.1$^{3,7}$]dec-2-ylidenemethyl)phenol was phosphorylated and then photooxygenated as described for its 5-chloro analog in Example X above. Work-up in 0.3% (w/v) aqueous sodium bicarbonate solution gave a filtered, aqueous solution of the crude 1,2-dioxetane phosphate salt, which was then subjected to reverse phase preparative HPLC (water-acetonitrile gradient) to give the syn- and anti-isomers, collected together, for lyophilization. When the lyophilized product, a white, fluffy solid, was subjected to analytical HPLC, two peaks were obtained with retention times of 8.52 and 8.94 minutes. The area percent ratio (270 nm) of the early eluting isomer to the later eluting isomer was found to be 0.5:1. $^1$HNMR confirmed that the product was a mixture of syn- and anti-disodium 3-(4-methoxyspiro-[1,2-dioxetane-3,2'-(5'-bromo)tricyclo[3.3.1.1$^{3,7}$]decan]-4-yl)phenyl phosphate.

$^1$HNMR (400 MHz, in D$_2$O, two isomers): δ6.99–7.52 (4H, m, ArH), 3.07 and 3.09 (3H, 2s, OMe), 2.91 (1H, br.s, H-1), 0.82–2.32 (12H, m).

EXAMPLE XII

Immunoassays for TSH were conducted on a series of TSH standards using a Hybritech Tandem-E TSH kit (Hybritech, Inc., San Diego, Calif.) according to the manufacturer's instructions included with the kit, except that upon completion of the anti-TSH-alkaline phosphatase conjugate incubation step and wash, the plastic beads were additionally washed with 0.1M diethanolamine, 1 mM magnesium chloride, 0.02% sodium azide buffer, pH 10.0, and then briefly stored in 200 μl of the same buffer.

Chemiluminescent signals from anti-TSH-alkaline phosphatase conjugate bound to the surface of the beads were initiated by adding to the tubes containing beads 300 μl of 0.67 mM buffer solutions containing, respectively, disodium 3-(2'-spiroadamantane)-4-methoxy-4-(3"-phosphoryloxy) phenyl-1,2-dioxetane ("AMPPD"), disodium 3-(4-methoxyspiro-[1,2-dioxetane-3,2'-(5'-hydroxy)tricyclo [3.3.1.1$^{3,7}$]decan]-4-yl)phenyl phosphate (A isomer; "A-OH-AMPPD"), the corresponding disodium B-isomer ("B-OH-AMPPD"), and disodium 3-(4-methoxyspiro-[1,2-dioxetane-3,2'-(5'-chloro)tricyclo[3.3.1.1$^{3,7}$]decan]-4-yl) phenyl phosphate ("Cl-AMPPD"), in 0.1M diethanolamine, 1 mM magnesium chloride, 0.02% sodium azide, pH 10.0. The intensity of light emission was subsequently recorded at 7, 13, 19, 25, 31, 40, 50 and 60 minutes after the substrate addition, as a 5 second integral at room temperature (about 25° C.), using a Berthold LB952T Luminometer (Berthold Instrument, Wildbad, Federal Republic of Germany).

TSH, RLU v. TSH for each of AMPPD, Br-AMPPD, B-OH-AMPPD, A-OH-AMPPD and Cl-AMPPD is shown in FIGS. 1, 2, 3, 4 and 5, respectively.

EXAMPLE XIII

A comparison of the total luminescence emission from AMPPD and from the corresponding 1,2-dioxetanes whose adamant-2'-ylidene groups are monosubstituted with hydroxy (A and B isomers), chloro and bromo groups was made by carrying out total dephosphorylation experiments on each of these compounds.

An aqueous solution of the 1,2-dioxetane (4.0 mM) in 0.05M sodium carbonate/sodium bicarbonate containing 1 mM magnesium chloride was prepared and then equilibrated at 30° C. Ten μl of a 7.64×10M aqueous solution of alkaline phosphatase (calf intestine; Biozyme) was then added, and the chemiluminescence from the resulting solution was recorded using a Turner Model 20E luminometer (Turner Instruments; Sunnyvale, Calif.).

The rates of chemiluminescence decay for each of the five compounds in question, expressed in relative light units (RLU's) per minute, are given in the following table.

TABLE I

| 1,2-Dioxetane | Decay Rate (RW's) | | | Total Decay Time (min). |
|---|---|---|---|---|
| | I | II | III | |
| AMPPD | 0.1 | 0.3 | 0.8 | 60 |
| OH-Adamant-2'--ylidene (A isomer) | 1.3 | — | — | 9 |
| OH-Adamant-2'--ylidene (B isomer) | 1.5 | — | — | 10 |
| Cl-Adamant-2'--ylidene | 1.2 | 5.5 | — | 15 |
| Br-Adamant-2'--ylidene | 1.2 | 0.8 | — | 40 |

These total chemiluminescence emissions are depicted graphically in FIGS. 6, 7, 8, 9 and 10, respectively.

EXAMPLE XIV

A strip of neutral BIODYNE A nylon membrane (Pall Corporation, Glen Cove, N.Y.) was dotted twice (side-byside) with the following concentrations of biotinylated pBr 322 35-mer oligonucleotide probe (Synthetic Genetics, San Diego, Calif.):

| Pair of Dots No. | DNA Concentration (picograms) |
|---|---|
| 1 | 100.000 |
| 2 | 50.000 |
| 3 | 25.000 |
| 4 | 12.500 |
| 5 | 6.250 |
| 6 | 3.125 |
| 7 | 1.563 |
| 8 | 0.781 |
| 9 | 0.391 |
| 10 | blank[1/] |

[1/]Single stranded, unlabeled DNA, 1 ng.

Next, the membrane was blocked in 0.2% casein/0.1% Tween 20 detergent in aqueous phosphate buffered saline solution (PBS) for 1 hour, following which 1/5000 diluted avidin-alkaline phosphatase conjugate (Sigma, Inc., St. Louis, Mo.) in 0.2% casein in PBS was added. The membrane was then incubated for 30 minutes, washed twice (for 5 minutes each time) in 0.2% casein/0.1% Tween 20 detergent in PBS, washed four times (for 5 minutes each time) in 0.3% Tween 20 detergent in PBS, and twice (for 5 minutes each time) in aqueous 0.1M diethanolamine containing 1 mM magnesium chloride, pH 10.0.

Figure 11:
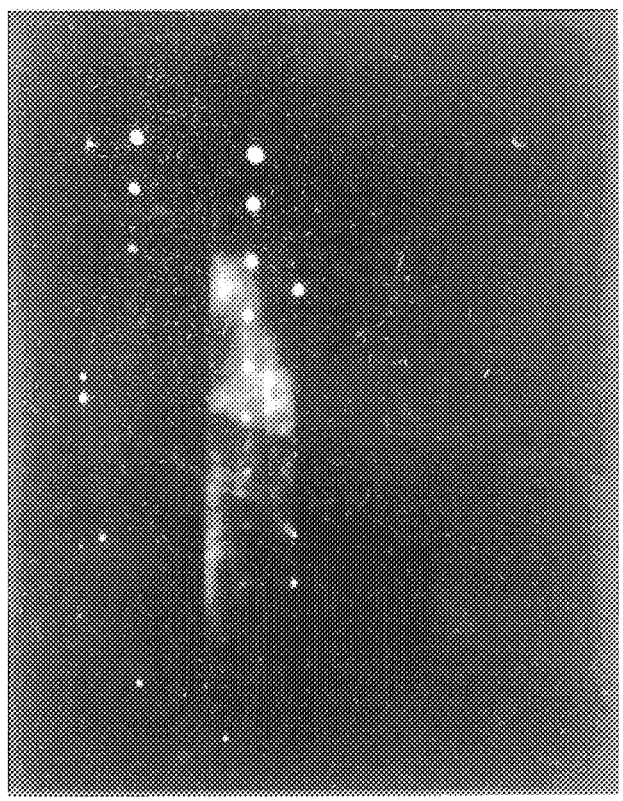
FIG. 11 shows the improved chemiluminescence intensity obtained using the chloroadamant-2'-ylidene analog of AMPPD as compared to AMPPD itself as the reporter molecule in a nucleic acid assay; see Example XIV below.

The membrane was then cut up the middle to give two strips, each bearing one set of dots. One of the strips was incubated for 5 minutes in aqueous AMPPD solution (0.25 mM in 0.1M diethanolamine containing 1 mM magnesium chloride, pH 10), the other for 5 minutes in the corresponding chloroadamant-2'-ylidene compound (0.25 mM in the same buffer). The two strips were then placed in camera luminometers and exposed on Polaroid Type 612 instant black and white film. The improved chemiluminescence intensity obtained using the chloro compound, as compared to AMPPD itself, can be seen by comparing column 2 (Cl-AMPPD) to column 1 AMPPD) in FIG. 11.

EXAMPLE XV pBr 322 plasmid (4700 bp) was subjected to a nick translation process using a Trans-Light kit (Tropix, Inc., Bedford, Mass.) to generate a mixture of biotinylated single stranded polynucleotides of 200–2000 bps in length.

This mixture was dotted onto a dry BIODYNE A membrane as five parallel columns of dots of the following concentrations:

| Row of Dots No. | DNA Concentration (picograms) |
|---|---|
| 1 | 20.000 |
| 2 | 10.000 |
| 3 | 5.000 |
| 4 | 2.500 |
| 5 | 1.250 |
| 6 | 0.625 |
| 7 | 0.313 |
| 8 | 0.156 |
| 9 | 0.078 |
| 10 | 0.039 |

The membrane was subjected to ultraviolet irradiation (UVP Mineral Light; UVP, San Gabriel, Calif.) for 3 minutes to fix the DNA to the surface of the membrane, then air dried. Next, the membrane was blocked in 0.2% casein/0.1% Tween 20 detergent in PBS for 1 hour, following which 1/5000 diluted avidin-alkaline phosphatase conjugate (Tropix, Inc.) in 0.2% casein in PBS was added. The membrane was then incubated for 30 minutes, washed three times (for 5 minutes each time) in 0.2% casein/0.1% Tween 20 detergent in PBS and washed once for five minutes in aqueous 0.1M diethanolamine containing 1 mM magnesium chloride and 0.02% sodium azide, pH 10.0 (substrate buffer).

Next, the five columns of rows of dots 1–5 were individually cut from the membrane ("strips 1–5"), as were the five columns of rows of dots 6–10 ("strips 6–10"). Strips 1–5 were washed with substrate buffer for 30 minutes. Strips 6–10 were blocked in 0.1% BDMQ in substrate buffer for 30 minutes. Both sets of strips were then incubated for 5 minutes in substrate buffer, then individually incubated for five minutes in aqueous solutions (0.25 mM) of 1,2-dioxetanes as indicated below:

| Strip No. | 1.2-Dioxetane |
|---|---|
| 1 | AMPPD |
| 2 | OH-Adamant-2'-ylidene (A isomer) |
| 3 | OH-Adamant-2'-ylidene (B isomer) |
| 4 | Cl-Adamant-2'-ylidene |
| 5 | Br-Adamant-2'-ylidene |
| 6 | AMPPD |
| 7 | OH-Adamant-2'-ylidene (A isomer) |
| 8 | OH-Adamant-2'-ylidene (B isomer) |
| 9 | Cl-Adamant-2'-ylidene |
| 10 | Br-Adamant-2'-ylidene |

All strips were then placed in camera luminometers and exposed on Polaroid Type 612 instant black and white film. The improved chemiluminescence intensity obtained using the 3-(substituted adamant-2'-ylidene)1,2-dioxetanes, as compared to AMPPD itself, can be seen from the results shown in Table II below.

TABLE II

ALKALINE PHOSPHATASE-LABELED DNA PROBE DETECTION IN MEMBRANE
WITH AND WITHOUT BDMQ BLOCKING STEP

| Membrane # | Dioxetane | BDMQ Blocking Step | Detection limit 5. min. exp.[1/] | (in picograms DNA) 1 min. exp.[2/] |
|---|---|---|---|---|
| 1 | AMPPD | no | 2.500 | 5.000 |
| 2 | OH-Adamant-2'-ylidene (A isomer) | no | 5.000 | 10.000 |

TABLE II-continued

ALKALINE PHOSPHATASE-LABELED DNA PROBE DETECTION IN MEMBRANE
WITH AND WITHOUT BDMQ BLOCKING STEP

| Membrane # | Dioxetane | BDMQ Blocking Step | Detection limit 5. min. exp.[1] | (in picograms DNA) 1 min. exp.[2] |
|---|---|---|---|---|
| 3 | OH-Adamant-2'-ylidene (B isomer) | no | 5.000 | 20.000 |
| 4 | CL-Adamant-2'-ylidene | no | 1.250 | 1.250 |
| 5 | Br-Adamant-2'-ylidene | no | 1.250 | 2.500 |
| 6 | AMPPD | BDMQ | 0.625 | 1.250 |
| 7 | OH-Adamant-2'-ylidene (A isomer) | BDMQ | 0.625 | 2.500 |
| 8 | OH-Adamant-2'-ylidene (B isomer) | BDMQ | 1.250 | 5.000 |
| 9 | Cl-Adamant-2'-ylidene | BDMQ | 0.313 | 0.313 |
| 10 | Br-Adamant-2'-ylidene | BDMQ | 0.313 | 0.313 |

[1] Five minute exposure was performed 40 minutes after dioxetane addition.
[2] One minute exposure was performed 77 minutes after dioxetane addition.

EXAMPLE XVI

A strip of neutral BIODYNE A nylon membrane was dotted twice (side-by-side) with 12.5 picograms of biotinylated pBR 322 35-mer oligonucleotide probe (Biogen, Inc., Cambridge, Mass.), dried, and subjected to ultraviolet radiation from an UVP Mineral Light lamp for 5 minutes to fix the DNA to the surface of the membrane. Next, the membrane was wetted with 5×SSC (0.015M sodium citrate/ 0.15M sodium chloride) and blocked in 0.2% casein, 0.1% Tween 20 detergent in PBS for 1 hour. The blocked membrane was then incubated with avidin-alkaline phosphatase conjugate ("Avidx" conjugate; Tropix, Inc.), diluted 1–10, 000 in 0.2% casein, for 30 minutes.

The membrane was then washed twice (for 5 minutes each time) with aqueous 0.2% casein/0.1% Tween 20 detergent, then twice (for 5 minutes each time) with aqueous 0.1% Tween 20 detergent in PBS, and finally twice (for 5 minutes each time) in aqueous 0.1M diethanolamine containing 1 mM magnesium chloride, pH 10 (assay buffer).

Figure 12:
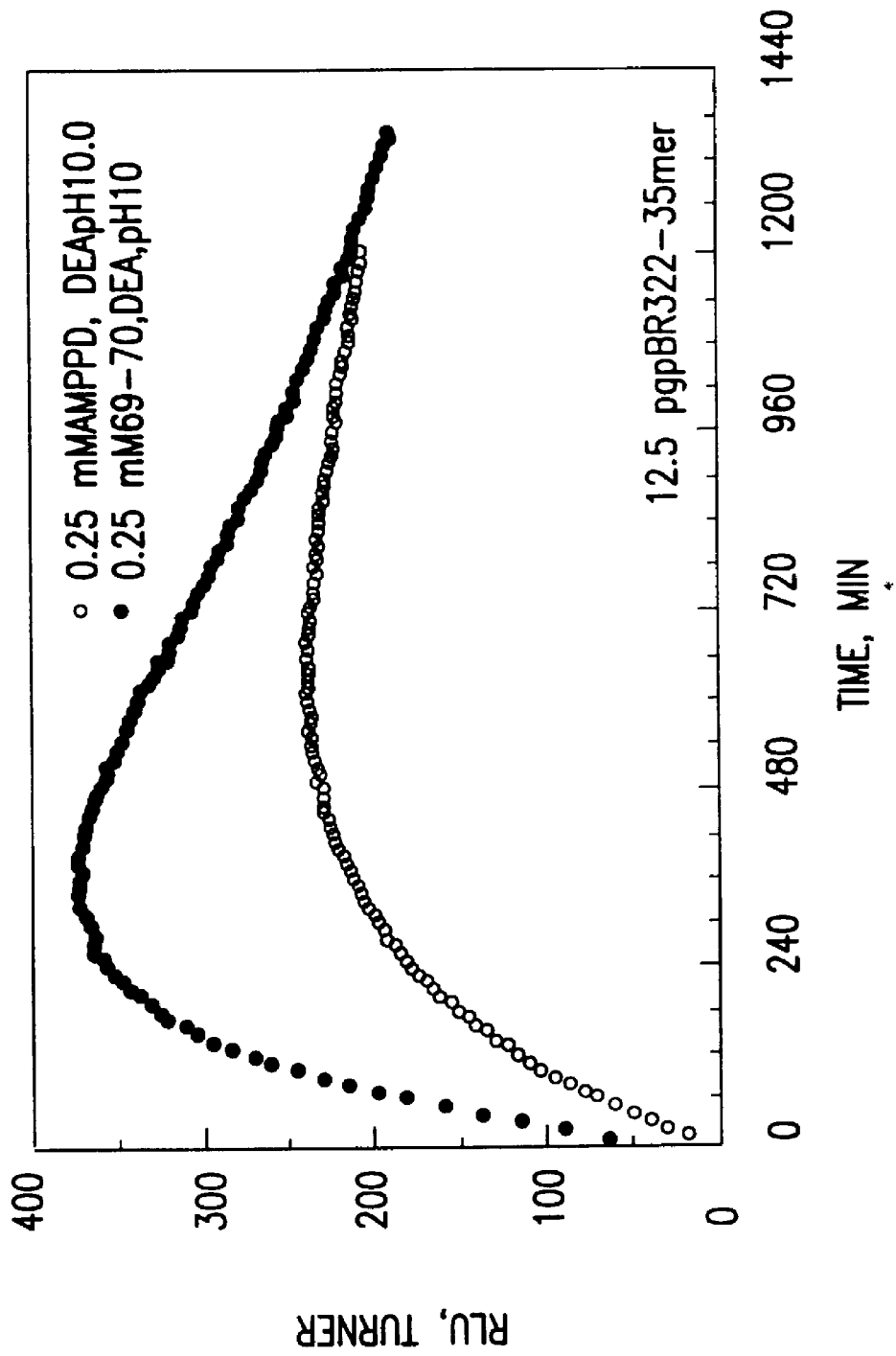
FIG. 12 shows the kinetics of the light emissions obtained using the chloroadamant-2'-ylidene analog of AMPPD and AMPPD itself as the reporter molecules in a nucleic acid assay; see Example XVI below.

The washed membrane was cut in half to give two strips, each bearing one dot. The strips were incubated, respectively, in aqueous 0.25 mM solutions of AMPPD and the corresponding chloroadamant-2'-ylidene compound in 0.1M diethanolamine containing 1 mM magnesium chloride, pH 10 for five minutes, then drained and sealed in plastic bags which were taped to the window of a Turner Model 20E luminometer. The chemiluminescence emission from each strip was integrated for 20 hours. The kinetics of the light emissions obtained are shown in FIG. 12.

EXAMPLE XVII

The enhancement of chemiluminescence emission (as compared to the emission from AMPPD) provided by the corresponding hydroxyadamant-2'-ylidene (A and B isomers) and chloroadamant-2'-ylidene compounds, all in the further presence of the enhancer polymers listed below, was demonstrated in the following manner.

Four sets of three tubes each, each tube in each set containing 450 $\mu$l of a 0.4 mM aqueous solution of one of the four 1,2-dioxetanes being compared in 0.1M diethanolamine containing 1 mM magnesium chloride, 0.02% sodium azide and 0.1% of the enhancer polymer, pH 10.0 (substrate buffer) were prepared and the background signal from each tube measured using a Berthold LB 952T luminometer (Berthold Instruments; Wildbad, Federal Republic of Germany).

Next, 50 $\mu$l of an aqueous solution, $2.83 \times 10^{-12}$M, of alkaline phosphatase in 0.1M diethanolamine containing 1 mM magnesium chloride, 0.02% sodium azide, pH 10.0, (final enzyme concentration $2.83 \times 10^{-13}$M) was added to each tube and the chemiluminescent signals were measured in the luminometer at 5 and 20 minutes. The intensity of the chemiluminescent signals and the signal: background ratios obtained for each of the four 1,2-dioxetanes in the presence of the enhancer polymers are shown in Table III below.

The enhancer polymers used, and the symbols for such polymers used in Table III, were the following:

TABLE III

| POLYMER | TIME | AMPPD SIGNAL | S/N | SIGNAL | S/N | SIGNAL | S/N | SIGNAL | S/N |
|---|---|---|---|---|---|---|---|---|---|
| NONE | 0 | 172.6 | 1.0 | 87.0 | 1.0 | 126.3 | 1.0 | 85.3 | 1.0 |
|  | 5 | 3706.0 | 21.6 | 2653.6 | 32.9 | 3314.8 | 26.3 | 4063.6 | 47.9 |
|  | 20 | 5944.8 | 34.4 | 3160.8 | 36.3 | 3767.9 | 29.8 | 4460.9 | 52.3 |
| SAPPHIRE | 0 | 241.4 | 1.0 | 86.1 | 1.0 | 138.8 | 1.0 | 296.0 | 1.0 |
|  | 5 | 38457.8 | 159.3 | 21051.3 | 244.5 | 10908.4 | 78.6 | 51584.5 | 371.6 |
|  | 20 | 85359.8 | 351.6 | 25130.3 | 292.3 | 14625.4 | 105.3 | 70161.6 | 505.4 |
| TMQ | 0 | 159.9 | 1.0 | 77.9 | 1.0 | 125.7 | 1.0 | 60.3 | 1.0 |
|  | 5 | 10525.8 | 65.8 | 8853.4 | 113.6 | 6258.9 | 49.8 | 9941.0 | 165.0 |
|  | 20 | 22558.3 | 141.1 | 11658.3 | 149.6 | 8857.8 | 70.5 | 13640.5 | 226.4 |
| S/TMQ(1:4) | 0 | 116.3 | 1.0 | 81.2 | 1.0 | 134.0 | 1.0 | 60.0 | 1.0 |
|  | 5 | 5931.5 | 35.7 | 9294.6 | 114.5 | 4775.3 | 35.6 | 5631.2 | 93.9 |
|  | 20 | 15866.3 | 95.4 | 1201.7 | 148.1 | 7120.3 | 53.1 | 9957.4 | 165.0 |

TABLE III-continued

| | | AMPPD | | | | | | | |
|---|---|---|---|---|---|---|---|---|---|
| POLYMER | TIME | SIGNAL | S/N | SIGNAL | S/N | SIGNAL | S/N | SIGNAL | S/N |
| S/TMQ(1:2) | 0 | 169.8 | 1.0 | 90.6 | 1.0 | 160.3 | 1.0 | 66.8 | 1.0 |
| | 5 | 3437.0 | 20.2 | 10193.8 | 112.5 | 3305.1 | 20.6 | 3121.4 | 46.7 |
| | 20 | 9994.7 | 58.9 | 11365.1 | 158.6 | 4722.3 | 35.7 | 6896.9 | 100.2 |
| DAA TMQ | 0 | 180.0 | 1.0 | 90.5 | 1.0 | 136.0 | 1.0 | 82.6 | 1.0 |
| | 5 | 8354.4 | 46.4 | 5583.1 | 61.7 | 5486.8 | 40.3 | 10326.7 | 125.1 |
| | 20 | 14957.3 | 83.1 | 6309.4 | 69.7 | 8670.3 | 49.0 | 13204.2 | 159.9 |
| DMQ TEQ | 0 | 245.2 | 1.0 | 90.8 | 1.0 | 145.5 | 1.0 | 77.2 | 1.0 |
| | 5 | 32820.5 | 133.9 | 17235.6 | 189.7 | 9213.8 | 63.3 | 39720.6 | 514.6 |
| | 20 | 78977.4 | 322.1 | 20702.2 | 227.9 | 8268.0 | 57.0 | 57658.0 | 747.2 |
| TEQ | 0 | 217.8 | 1.0 | 348.8 | 1.0 | 142.6 | 1.0 | 67.1 | 1.0 |
| | 5 | 25095.8 | 115.3 | 15779.8 | 45.24 | 8806.2 | 61.8 | 26551.0 | 397.0 |
| | 20 | 50020.0 | 229.7 | 1906.9 | 54.7 | 11563.4 | 81.1 | 34467.2 | 513.5 |
| TBQ | 0 | 493.9 | 1.0 | 101.8 | 1.0 | 148.9 | 1.0 | 118.8 | 1.0 |
| | 5 | 94429.4 | 191.2 | 37244.5 | 366.0 | 15508.5 | 97.6 | 148394.5 | 1249.6 |
| | 20 | 214319.4 | 433.9 | 44569.8 | 430.0 | 20630.8 | 131.1 | 209466.8 | 1763.2 |
| MPS | 0 | 211.8 | 1.0 | 93.6 | 1.0 | 140.3 | 1.0 | 86.0 | 1.0 |
| | 5 | 19971.8 | 94.3 | 13165.3 | 140.7 | 10021.3 | 71.5 | 22170.5 | 257.8 |
| | 20 | 41701.8 | 196.9 | 16159.2 | 172.7 | 10939.0 | 78.0 | 29133.9 | 308.5 |
| BAEDM | 0 | 217.3 | 1.0 | 95.6 | 1.0 | 161.4 | 1.0 | 88.9 | 1.0 |
| | 5 | 9275.3 | 107.6 | 4887.3 | 61.6 | 4101.3 | 25.4 | 9066.9 | 102.2 |
| | 20 | 26529.1 | 308.5 | 7433.5 | 77.8 | 5538.2 | 34.3 | 17185.4 | 193.3 |
| BZ | 0 | 149.4 | 1.0 | 79.9 | 1.0 | 119.4 | 1.0 | | |
| | 5 | 2738.0 | 18.3 | 2156.9 | 27.0 | 2246.4 | 18.8 | | |
| | 20 | 4611.5 | 30.9 | 2536.7 | 31.7 | 2669.2 | 22.4 | | |
| DMEB | 0 | 176.6 | 1.0 | 79.9 | 1.0 | 124.6 | 1.0 | | |
| | 5 | 9401.5 | 52.6 | 6160.6 | 77.1 | 4451.6 | 35.7 | | |
| | 20 | 20434.9 | 114.4 | 7835.2 | 98.1 | 6023.9 | 48.3 | | |
| DME(OH)B | 0 | 161.6 | 1.0 | 85.2 | 1.0 | 132.1 | 1.0 | | |
| | 5 | 3462.3 | 21.4 | 3931.9 | 46.1 | 2640.9 | 20.0 | | |
| | 20 | 8540.9 | 52.9 | 5300.5 | 66.2 | 3990.6 | 30.2 | | |
| EMERALD | 0 | 2902.1 | 1.0 | | | | | 3434.0 | 1.0 |
| | 5 | 317571.6 | 109.4 | | | | | 400510.8 | 583.2 |
| | 20 | 818775.8 | 282.1 | | | | | 662054.4 | 964.0 |
| TBQ-FLUOR | 0 | 4961.2 | 1.0 | | | | | 5882.7 | 1.0 |
| | 5 | 57271.6 | 113.9 | | | | | 987572.0 | 839.4 |
| | 20 | 1445675.6 | 291.4 | | | | | 1505971.2 | 1280.0 |

| SYMBOL | ENHANCER POLYMER |
|---|---|
| SAPPHIRE | BDMQ |
| TMQ | poly(vinylbenzyltrimethylammonium chloride |
| S/TMQ | styrene/TMQ copolymer |
| DAA/TMQ | diacetone acrylamide/TMQ copolymer |
| DMQ/TEQ | poly(vinylbenzyldodecyldimethylammonium chloride)/TEQ copolymer |
| TEQ | poly(vinylbenzyltriethylammonium chloride) |
| TBQ | poly(vinylbenzyltributylammonium chloride) |
| MPB | poly(vinylbenzyl-N-methylpiperidinium chloride) |
| BAEDM | poly[vinylbenzyl(2-benzoylamino)ethyl-dimethylammonium chloride] |
| BZ | benzal mordant |
| DMEB | poly(vinylbenzyldimethylethyl-ammonium chloride) |
| DME(OH)B | poly[vinylbenzyldimethyl(2-hydroxy)eth-ylammonium chloride] |
| EMERALD | sapphire and fluorescein |
| TBQ/FLUOR | TBQ and fluorescein |

EXAMPLE XVIII

The background signals and t½ parameters (as compared to those of AMPPD) obtained for the substituted adamant-2'-ylidene compounds listed below in two different buffers were determined in the following manner.

Aqueous $4 \times 10^{-4}$M solutions of the 1,2-dioxetanes in a buffer solution made up of 0.05M sodium carbonate/sodium bicarbonate containing 1 mM magnesium chloride, pH 9.5, were prepared, as were aqueous $4 \times 10^{-4}$M solutions of the 1,2-dioxetanes in a buffer solution made up of 0.1M diethanolamine containing 1 mM magnesium chloride and 0.02% sodium azide, pH 10.0. One ml per tube of each of these solutions was placed in a Turner Model 20E luminometer and the background signals were measured.

Next, t½ values were measured for each sample as follows. One hundred $\mu$l of sample dioxetane in 900 $\mu$l of one of the above-described buffer solutions was pipetted into a tube (final dioxetane concentration $4 \times 10^{-5}$M) and equilibrated at 30° C. Ten $\mu$l of a 1–1,000 dilution of calf intestine alkaline phosphatase in the same buffer (enzyme concentration $7.6 \times 10^{-10}$M) was then added, and the resulting chemiluminescent intensity was recorded, using a Turner Model 20E luminometer, over a 30 minute period. T½ values were then calculated from the decay curves. The results of these determinations are given in Table IV below.

TABLE IV

| DIOXETANE | BACKGROUND AT 0.4 mM (TLU) | HALF LIFE OF ANION (min.) |
|---|---|---|
| 1. 0.05M Sodium Carbonate/Sodium Bicarbonate, 1 mM Magnesium Chloride, pH 9.5 | | |
| AMPPD | 1.96 | 2.42 |
| A-OH-AMPPD | 1.20 | 1.33 |
| B-OH-AMPPD | 1.72 | 1.49 |
| Cl-AMPPD | 0.93 | 1.08 |
| Br-AMPPD | 1.35 | 0.99 |
| 2. 0.1M Diethanolamine, 1 mM Magnesium Chloride, 0.02% Sodium Azide, pH 10.0 | | |
| AMPPD | 2.09 | 2.26 |
| A-OH-AMPPD | 0.95 | 1.05 |
| B-OH-AMPPD | 1.32 | 1.31 |
| Cl-AMPPD | 0.77 | 0.86 |
| Br-AMPPD | 1.13 | 0.56 |

EXAMPLE XIX

Alkaline phosphatase (calf intestine; Biozyme) was diluted 1–1,000,000 to generate a stock solution, concentration $2.54\times10^{-12}$M. A series of tubes was prepared, in duplicate, containing 450 µl of an aqueous 0.1M diethanolamine solution containing 1 mM magnesium chloride and 0.02% sodium azide, pH 10, plus 0.1% of one of the enhancer polymers specified below and $4.4\times10^{-4}$M of a 1,2-dioxetane: AMPPD or the corresponding chloroadamant-2'-ylidene compound.

Fifty µl of alkaline phosphatase stock solution was then added to give samples containing the following enzyme concentrations:

$2.54\times10^{-12}$M
$8.49\times10^{-13}$M
$2.83\times10^{-13}$M
$9.45\times10^{-14}$M
$3.15\times10^{-14}$M
$1.05\times10^{-14}$M
$3.49\times10^{-15}$M
$1.16\times10^{-15}$M
$3.88\times10^{-16}$M
$1.29\times10^{-16}$M
$4.31\times10^{-17}$M The final concentration of 1,2-dioxetane in each tube was $4\times10^{-4}$M; the final concentration of enhancer polymer was 0.09%. Five second integrals were recorded at 5 and 20 minutes following 1,2-dioxetane addition.

Figure 13:
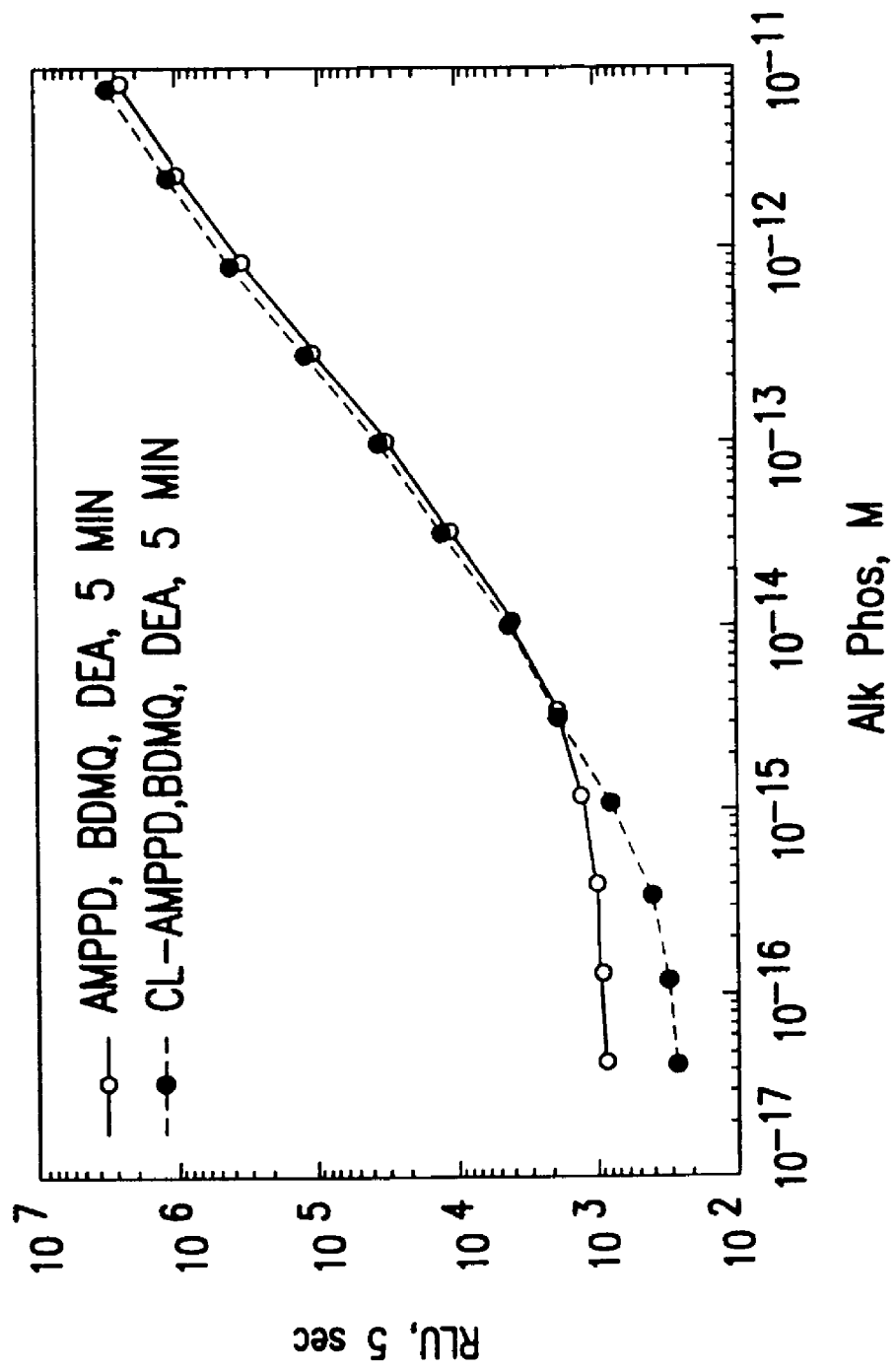
FIG. 13 is the dose response curve at five minutes for alkaline phosphatase dilution with the chloroadamant-2'-ylidene analog of AMPPD plus poly[vinyl (benzyldimethylammonium chloride)] ("BDMQ"), compared to the dose response curve at five minutes for AMPPD itself plus BDMQ; see Example XIX below.
Figure 14:
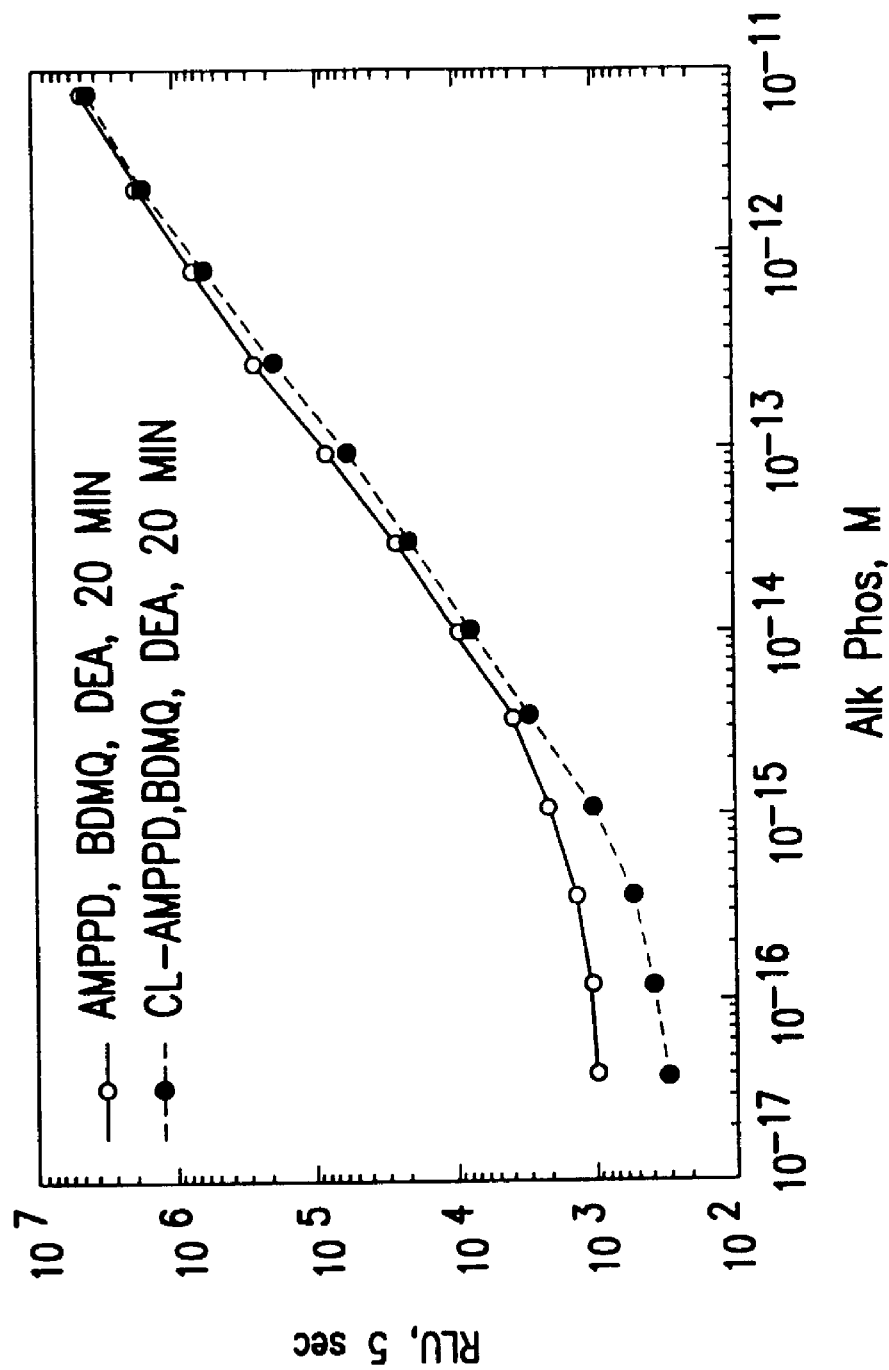
FIG. 14 is the dose response curves at 20 minutes for the same substances whose dose response curves are shown in FIG. 13.
Figure 15:
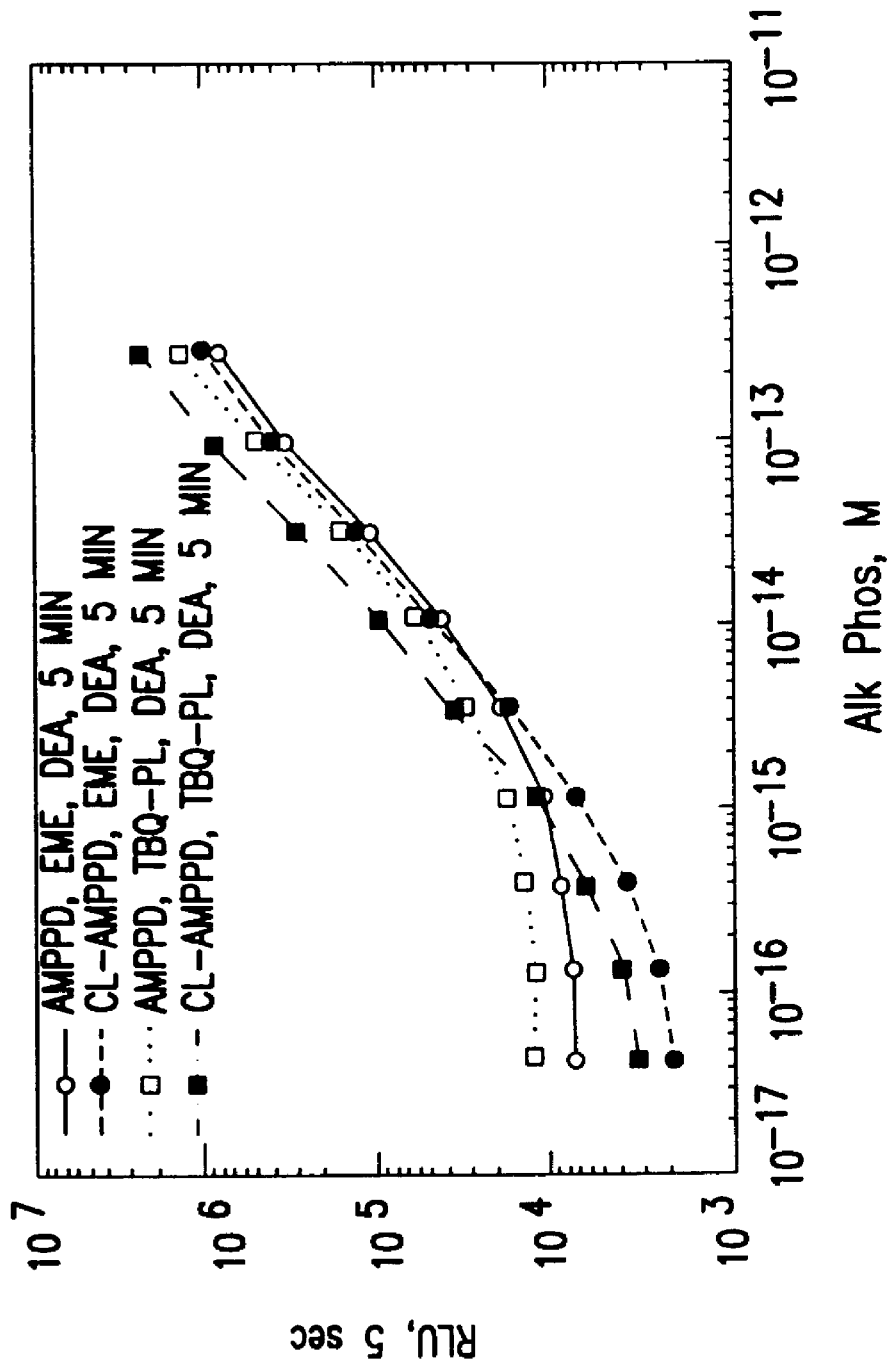
FIG. 15 is the dose response curve at five minutes for alkaline phosphatase dilution with the chloroadamant-2'-ylidene analog of AMPPD plus BDMQ-fluorescein ("emerald"), compared to the dose response curve at five minutes for AMPPD itself plus emerald; again see Example XIX below.
Figure 16:
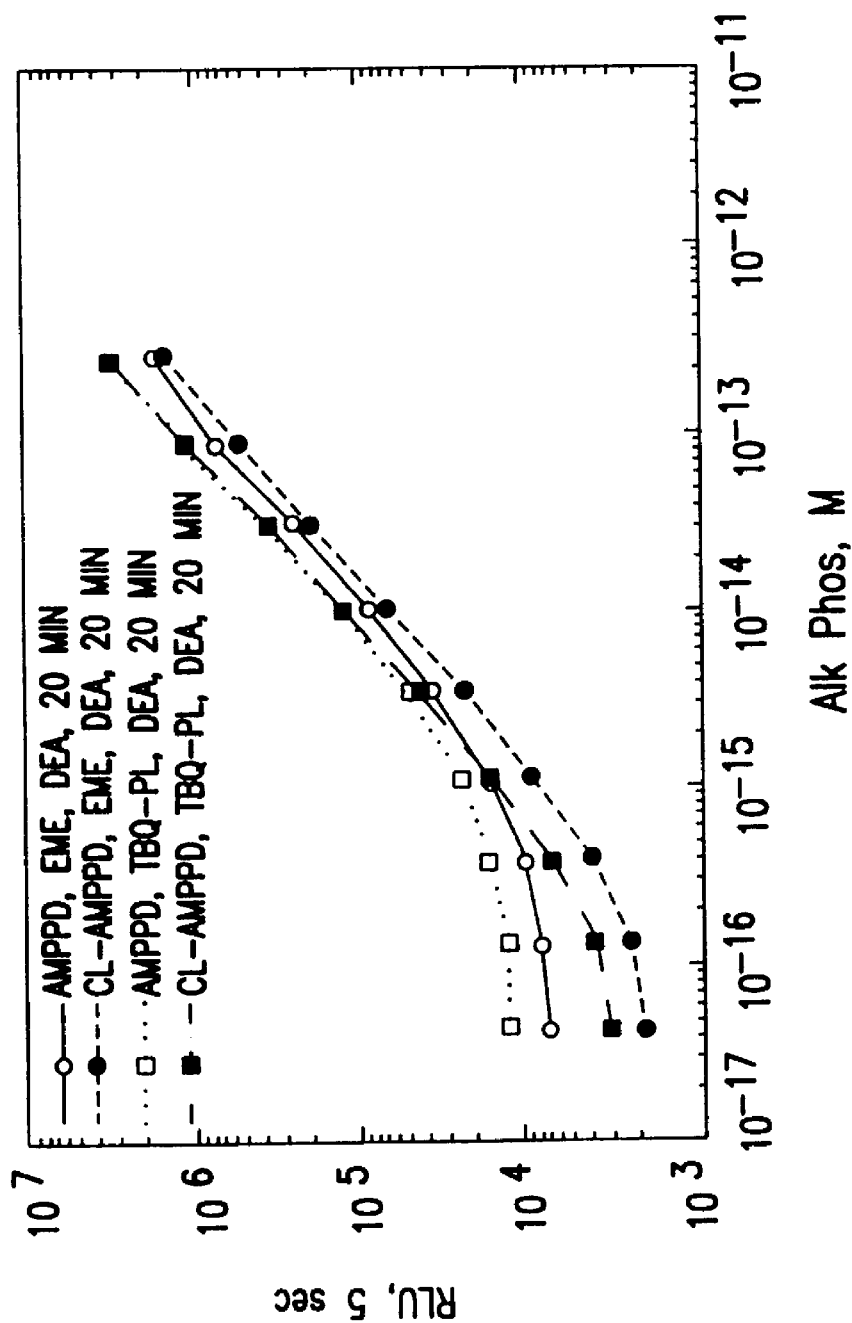
FIG. 16 is the dose response curves at 20 minutes for the same substances whose dose response curves are shown in FIG. 15.

FIGS. 13 and 14 are dose response curves for alkaline phosphatase dilution with the chloroadamant-2'-ylidene 1,2-dioxetane plus BDMQ at 5 and 20 minutes after dioxetane addition, as compared to the dose response curves for AMPPD plus BDMQ. FIGS. 15 and 16 show alkaline phosphatase dilutions detected with the chloroadamant-2'-ylidene 1,2-dioxetane plus BDMQ-fluorescein ("emerald") and poly(vinylbenzyltributylammonium chloride) ("TBQ") -fluorescein, at 5 and 20 minutes after substrate addition, as compared to AMPPD plus the same enhancer polymers.

EXAMPLE XX pBR 322 plasmid (Biogen, Inc., Cambridge, Mass.) containing an insert of TPA sequence was digested with MSP1 restriction enzyme. Chemical cleavages were performed as described in Maxam, et al., PNAS, 74, 560 (1977) to yield G, AG, AC, TC and C—and one other, T,—as described by Rubin, et al., Nucleic Acids Research, 8, 4613 (1980). One seventh of each reaction tube's contents was loaded per lane onto 0.4 mm TBE-gradient sequencing gel (60 cm in length). After 4 hours of electrophoresis, DNA was electrotransferred to a BIODYNE A nylon membrane (0.45 µm) and treated with ultraviolet light to fix the DNA to the membrane's surface.

Next, the membrane was dried, prehybridized for 30 minutes at 45° C. in aqueous buffer solution containing 1% BSA, 0.5M sodium phosphate and 7% SDS, pH 7.2, then hybridized for 2 hours at 45° C. with 10 µl of NNB snap direct alkaline phosphatase conjugated probe (Molecular Biosystems, Inc., San Diego, Calif.) in 40 ml of the above-described BSA buffer solution. The membrane was then washed twice in aqueous 5×SSC/1% SDS (for 5 minutes each time) at 45° C., twice in aqueous 1×SSC/1% SDS (for 5 minutes each time) at 45° C., once in an aqueous solution containing 125 mM sodium chloride, 50 mM Tris and 1% Triton X-100 detergent, pH 8.0, twice in aqueous 1×SSC (for 1 minute each time) at room temperature, and finally twice (for one minute each time) at room temperature in an aqueous solution containing 0.1M diethanolamine, 1 mM magnesium chloride and 0.02% sodium azide at pH 10.0.

The membrane was then wetted with aqueous AMPPD solution (0.25 mM), wrapped in Saran wrap, and exposed to Kodak XAR X-ray film for 40 minutes. A five minute exposure was then taken 1 hour after AMPPD addition. The sequence images are shown in FIG. 17(1).

Figure 17:
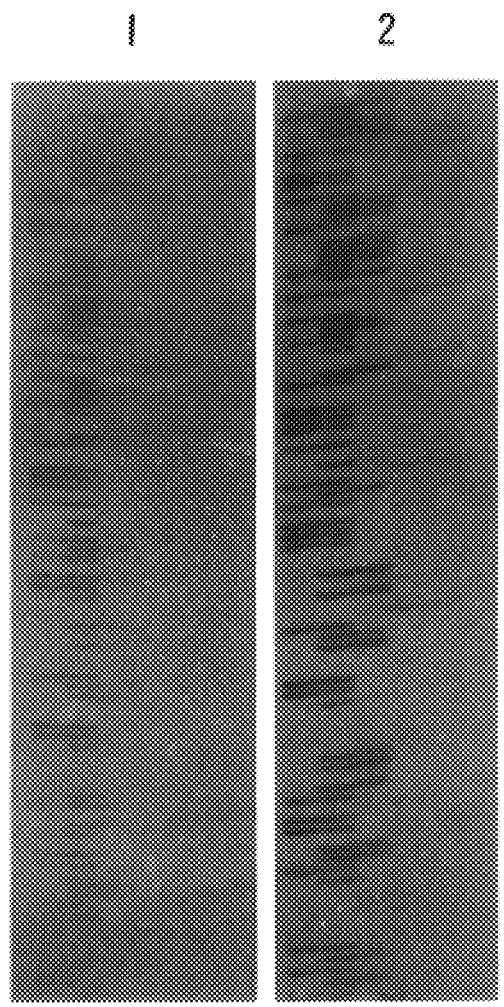
FIG. 17 shows a TPA sequence's images, obtained as described in Example XX below using (1) AMPPD and (2) AMPPD's chloroadamant-2'-ylidene analog.

Repeating this entire procedure using the corresponding chloroadamant-2'-ylidene 1,2-dioxetane compound gave the sequence images shown in FIG. 17(2).

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

We claim:

1. An enol ether of the formula:

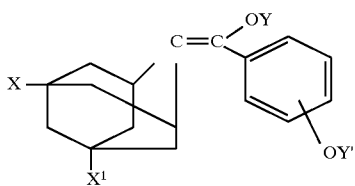

wherein:

X and $X^1$ each represent, individually, hydrogen, a hydroxyl group, a halo substituent, an unsubstituted lower alkyl group, a hydroxy (lower) alkyl group, a halo (lower) alkyl group, a phenyl group, a halophenyl group, an alkoxyphenyl group, a hydroxyalkoxy group, a cyano group or an amide group, with at least one of X and $X^1$ being other than hydrogen;

Y represents a lower alkyl group; and

Y' represents hydrogen, a lower alkyl group, a lower alkenyl group, an aralkyl group having up to 20 carbon atoms, an alkali metal cation an acyl group having from two to about 14 carbon atoms, inclusive,

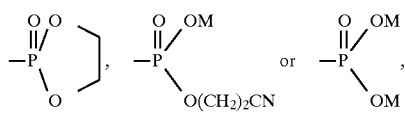

an alkali metal cation, where M represents, independently, a proton, an alkali metal cation, ammonium, substituted ammonium, quaternary ammonium or an $H^+$ pyridinium cation.

2. A compound of claim 1 wherein X is hydroxyl and $X^1$ is hydrogen.

3. A compound of claim 1 wherein X is chloro and $X^1$ is hydrogen.

4. A compound of claim 1 wherein X is bromo and $X^1$ is hydrogen.

5. A compound of any one of claims 2–4, inclusive, wherein Y is methyl.

6. A compound of claim 5 wherein $Y^1$ is

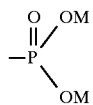

7. A compound of claim 6 wherein each M is sodium.

8. Disodium 3-(methoxy-5-hydroxytricyclo[$3.3.1.1^{3,7}$]dec-2-ylidenemethyl)phenyl phosphate.

9. Disodium 3-(methoxy-5-chlorotricyclo[$3.3.1.1^{3,7}$]dec-2-ylidenemethyl)phenyl phosphate.

10. Disodium 3-(methoxy-5-bromotricyclo[$3.3.1.1^{3,7}$]dec-2-ylidenemethyl)phenyl phosphate.

11. The enol ether of claim 1, wherein Y is a $C_1$–$C_{20}$ alkyl substituted with a perfluoralkyl group of 1–7 carbon atoms.

12. The enol ether of claim 11, wherein Y is a lower alkyl substituted with a trifluoromethyl group.

13. The enol ether of claim 12, wherein Y is a $C_1$ alkyl.

14. A dioxetane of the formula

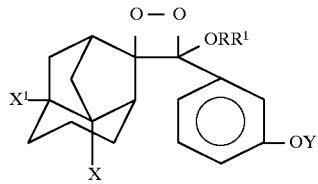

wherein X and $X^1$ each represent, individually, hydrogen, a hydroxyl group, a halo substituent, a hydroxy (lower) alkyl group, a halo (lower) alkyl group, a phenyl group, a halophenyl group, an alkoxyphenyl group, a hydroxyalkoxy group, a cyano group or an amide group, with at least one of X and $X^1$ being other than hydrogen;

wherein Y is a moiety selected from the group consisting of a phosphate, galactoside, acetate, 1-phospho-2,3-diacylglyceride, 1-thio-D-glucoside, adenosine triphosphate, adenosine diphosphate, adenosine monophosphate, adenosine, alpha-D-glucoside, beta-D-glucoside, alpha-D-mannoside, beta-D-mannoside, beta-D-fructofuranoside, beta-D-glucosiduronate, p-toluenesulfonyl-L-arginine ester, and p-toluenesulfonyl-1-arginine amide;

wherein R is a $C_1$–$C_{20}$ alkyl group; and wherein $R^1$ is a perfluoralkyl group of 1–7 carbon atoms.

15. The dioxetane of claim 14, wherein R is $C_1$ alkyl.

16. The dioxetane of claim 15, wherein $R^1$ is trifluoromethyl.

* * * * *